United States Patent
Oral et al.

(10) Patent No.: US 12,350,403 B2
(45) Date of Patent: Jul. 8, 2025

(54) METHODS OF MAKING THERAPEUTIC POLYMERIC MATERIAL

(71) Applicant: THE GENERAL HOSPITAL CORPORATION, Boston, MA (US)

(72) Inventors: Ebru Oral, Newton, MA (US); Jeremy V. Suhardi, Boston, MA (US); Orhun K. Muratoglu, Cambridge, MA (US); Henrik Malchau, Cambridge, MA (US); Harry E. Rubash, Marco Island, FL (US); Andrew A. Freiberg, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 203 days.

(21) Appl. No.: 15/774,860

(22) PCT Filed: Nov. 10, 2016

(86) PCT No.: PCT/US2016/061256
§ 371 (c)(1),
(2) Date: May 9, 2018

(87) PCT Pub. No.: WO2017/083476
PCT Pub. Date: May 18, 2017

(65) Prior Publication Data
US 2018/0318468 A1 Nov. 8, 2018

Related U.S. Application Data

(60) Provisional application No. 62/254,409, filed on Nov. 12, 2015.

(51) Int. Cl.
*A61L 27/54* (2006.01)
*A61F 2/34* (2006.01)
(Continued)

(52) U.S. Cl.
CPC .......... *A61L 27/54* (2013.01); *A61F 2/34* (2013.01); *A61F 2/389* (2013.01); *A61F 2/4081* (2013.01);
(Continued)

(58) Field of Classification Search
CPC .......... B32B 3/00; A61L 31/048; A61L 31/16; A61L 27/54; A61K 38/14; A61K 47/34; B29C 35/08; C08J 3/28
See application file for complete search history.

(56) References Cited

U.S. PATENT DOCUMENTS

| 3,974,132 | A | 8/1976 | Valdiserri |
| 5,032,450 | A | 7/1991 | Rechlicz et al. |

(Continued)

FOREIGN PATENT DOCUMENTS

| EP | 1457172 A1 | 9/2004 |
| EP | 0881919 B1 | 8/2005 |

(Continued)

OTHER PUBLICATIONS

Ajandouz et al. "Effects of pH on Caramelization and Maillard Reaction Kinetics in Fructose-Lysine Model ISystems" 2001, J. Food Sci. 66(7):926-931.

(Continued)

*Primary Examiner* — Dah-Wei D. Yuan
*Assistant Examiner* — Andrew J Bowman
(74) *Attorney, Agent, or Firm* — McCarter & English, LLP

(57) ABSTRACT

Therapeutic polymeric materials, therapeutic polymeric materials containing medical implants and methods for making the same, and related materials are described. Methods of making medical implants containing additives/antibiotics, therapeutic polymers, and materials used therewith also are described. Methods of spatially controlling additive/

(Continued)

Fluorescent antibody staining for vancomycin on UHMWPE without additives (control), vancomycin-blended UHMWPE in its unirradiated form (VPE unirradiated) or after irradiation at 25-40 kGy (VPE irradiated). Green color indicating vancomycin presence is shown inside the dashed white lines.

antibiotic concentrations, non-homogenous distribution of therapeutic agents in polymeric materials and therapeutic medical implants containing layered constructs of polymeric materials are provided. Therapeutic medical implants containing incorporated therapeutic agents in the polymeric materials, for example, antibiotics into polymeric total joint implants, are useful for delivery of the therapeutic agents into the surrounding mediums.

8 Claims, 16 Drawing Sheets

(51) Int. Cl.
 *A61F 2/38*  (2006.01)
 *A61F 2/40*  (2006.01)
 *A61L 27/04*  (2006.01)
 *A61L 27/16*  (2006.01)
 *A61L 27/26*  (2006.01)
 *A61F 2/30*  (2006.01)

(52) U.S. Cl.
 CPC ............... *A61L 27/04* (2013.01); *A61L 27/16* (2013.01); *A61L 27/26* (2013.01); *A61F 2002/30677* (2013.01); *A61F 2002/30971* (2013.01); *A61L 2300/406* (2013.01); *A61L 2300/428* (2013.01); *A61L 2300/608* (2013.01); *A61L 2300/61* (2013.01); *A61L 2420/02* (2013.01); *A61L 2420/04* (2013.01); *A61L 2420/06* (2013.01); *A61L 2420/08* (2013.01); *A61L 2430/24* (2013.01)

(56) References Cited

U.S. PATENT DOCUMENTS

| | | | |
|---|---|---|---|
| 5,096,654 | A | 3/1992 | Craggs et al. |
| 5,827,904 | A | 10/1998 | Hahn |
| 5,879,400 | A | 3/1999 | Merrill et al. |
| 6,165,220 | A | 12/2000 | McKellop et al. |
| 6,316,158 | B1 | 11/2001 | Saum et al. |
| 6,448,315 | B1 | 9/2002 | Lidgren et al. |
| 6,641,617 | B1 | 11/2003 | Merrill et al. |
| 6,852,772 | B2 | 2/2005 | Muratoglu et al. |
| 6,951,654 | B2 | 10/2005 | Malcolm et al. |
| 7,205,339 | B2 | 4/2007 | Muratoglu |
| 7,381,752 | B2 | 6/2008 | Guard et al. |
| 7,431,874 | B2 | 10/2008 | Muratoglu et al. |
| 7,790,779 | B2 | 9/2010 | Muratoglu |
| 7,833,452 | B2 | 11/2010 | Muratoglu et al. |
| 7,858,671 | B2 | 12/2010 | Merrill et al. |
| 8,133,501 | B2 | 3/2012 | Li et al. |
| 8,232,322 | B2 | 7/2012 | East et al. |
| 8,420,000 | B2 | 4/2013 | Muratoglu et al. |
| 8,425,815 | B2 | 4/2013 | Muratoglu et al. |
| 8,461,225 | B2 | 6/2013 | Muratoglu et al. |
| 8,529,937 | B2 | 9/2013 | Brunner et al. |
| 8,530,057 | B2 | 9/2013 | Muratoglu et al. |
| 8,569,395 | B2 | 10/2013 | Muratoglu et al. |
| 8,858,979 | B1 | 10/2014 | Desjardins et al. |
| 8,933,145 | B2 | 1/2015 | Oral et al. |
| 9,168,683 | B2 | 10/2015 | Muratoglu et al. |
| 9,220,811 | B2 | 12/2015 | Overstreet et al. |
| 9,273,189 | B2 | 3/2016 | Muratoglu et al. |
| 9,370,878 | B2 | 6/2016 | Muratoglu et al. |
| 9,433,705 | B2 | 9/2016 | Muratoglu et al. |
| 9,445,901 | B2 | 9/2016 | Tunc et al. |
| 9,681,683 | B2 | 6/2017 | Esposti et al. |
| 9,731,047 | B2 | 8/2017 | Oral et al. |
| 9,937,278 | B2 | 4/2018 | Steinberg et al. |
| 9,968,709 | B2 | 5/2018 | Muratoglu et al. |
| 10,220,547 | B2 | 3/2019 | Muratoglu et al. |
| 10,967,100 | B2 | 4/2021 | Oral et al. |
| 10,981,302 | B2 | 4/2021 | Muratoglu et al. |
| 11,970,600 | B2 | 4/2024 | Muratoglu et al. |
| 2002/0064653 | A1 | 5/2002 | Ladika |
| 2002/0107330 | A1 | 8/2002 | Pinchuk et al. |
| 2004/0156879 | A1 | 8/2004 | Muratoglu et al. |
| 2004/0180072 | A1 | 9/2004 | Tunc et al. |
| 2005/0048121 | A1* | 3/2005 | East ................. A61L 27/54 424/486 |
| 2005/0090571 | A1 | 4/2005 | Mehta et al. |
| 2005/0271694 | A1* | 12/2005 | Mansouri ............ A61L 31/16 427/2.24 |
| 2006/0064653 | A1 | 3/2006 | Zhang et al. |
| 2007/0059334 | A1 | 3/2007 | Abt et al. |
| 2007/0077268 | A1 | 4/2007 | King et al. |
| 2007/0114702 | A1 | 5/2007 | Muratoglu et al. |
| 2007/0141106 | A1 | 6/2007 | Bonutti et al. |
| 2007/0213835 | A1 | 9/2007 | Wimmer et al. |
| 2007/0265369 | A1 | 11/2007 | Muratoglu |
| 2007/0267030 | A1 | 11/2007 | Muratoglu et al. |
| 2007/0293647 | A1 | 12/2007 | McKellop et al. |
| 2008/0215142 | A1 | 9/2008 | Muratoglu et al. |
| 2008/0319137 | A1 | 12/2008 | Rufner et al. |
| 2009/0030524 | A1 | 1/2009 | Schroeder et al. |
| 2009/0118390 | A1* | 5/2009 | Abt ................. A61K 31/355 523/115 |
| 2009/0181253 | A1 | 7/2009 | Michalik et al. |
| 2009/0243159 | A1 | 10/2009 | Sun |
| 2009/0263319 | A1 | 10/2009 | Wohabrebbi et al. |
| 2010/0190882 | A1 | 7/2010 | Muratoglu et al. |
| 2010/0292374 | A1 | 11/2010 | Bellare |
| 2011/0039014 | A1 | 2/2011 | King |
| 2011/0040381 | A1 | 2/2011 | Kidd et al. |
| 2011/0070454 | A1 | 3/2011 | Gregg et al. |
| 2012/0041094 | A1* | 2/2012 | Oral ................... A61L 29/143 522/75 |
| 2012/0046380 | A1 | 2/2012 | Morrison et al. |
| 2012/0052292 | A1* | 3/2012 | Pulapura ............. A61L 31/10 428/336 |
| 2012/0267819 | A1 | 10/2012 | Freedman |
| 2013/0203885 | A1 | 8/2013 | Muratoglu et al. |
| 2014/0024736 | A1* | 1/2014 | Thomas ............. A61L 27/16 522/116 |
| 2014/0098001 | A1 | 4/2014 | Van Oosterbosch et al. |
| 2014/0175693 | A1 | 6/2014 | Liu |
| 2015/0151866 | A1 | 6/2015 | Oral |
| 2015/0190545 | A1 | 7/2015 | Oral |
| 2015/0290280 | A1* | 10/2015 | Petrak ............. A61L 27/16 604/151 |
| 2015/0314038 | A1 | 11/2015 | Oral et al. |
| 2016/0215117 | A1* | 7/2016 | Muratoglu ........... C08K 5/1545 |
| 2016/0250779 | A1 | 9/2016 | Muratoglu |
| 2017/0049934 | A1 | 2/2017 | Muratoglu et al. |
| 2017/0137603 | A1 | 5/2017 | Morrison et al. |
| 2017/0259467 | A1 | 9/2017 | Muratoglu et al. |
| 2018/0161480 | A1 | 6/2018 | Oral et al. |
| 2019/0134273 | A1 | 5/2019 | Oral et al. |
| 2019/0160207 | A1 | 5/2019 | Suhardi et al. |
| 2019/0255744 | A1 | 8/2019 | Muratoglu et al. |
| 2021/0228775 | A1 | 7/2021 | Oral et al. |
| 2024/0240005 | A1 | 7/2024 | Muratoglu et al. |

FOREIGN PATENT DOCUMENTS

| | | | |
|---|---|---|---|
| EP | 1779877 A1 | 5/2007 | |
| EP | 2384774 A2 | 11/2011 | |
| EP | 2833981 A2 | 2/2015 | |
| WO | 1997/029793 A1 | 8/1997 | |
| WO | 1999029793 A1 | 6/1999 | |
| WO | 2001005337 A1 | 1/2001 | |
| WO | 2001080778 A1 | 11/2001 | |
| WO | WO02/00274 | * 3/2002 | ............. A61L 27/54 |
| WO | 2002/048259 A2 | 6/2002 | |
| WO | 2005/074619 A2 | 8/2005 | |
| WO | 2005/110276 A1 | 11/2005 | |
| WO | 2006/026040 A1 | 3/2006 | |
| WO | 2007/024689 A2 | 3/2007 | |
| WO | 2007024684 A2 | 3/2007 | |
| WO | WO 2007/056667 | 5/2007 | |

(56) References Cited

FOREIGN PATENT DOCUMENTS

| WO | 2007139744 | A2 | 12/2007 | | |
|---|---|---|---|---|---|
| WO | 2008092047 | A1 | 7/2008 | | |
| WO | 2008109098 | A2 | 9/2008 | | |
| WO | 2010096771 | A2 | 8/2010 | | |
| WO | WO2012061499 | * | 5/2012 | ............ | A61L 27/16 |
| WO | 2013/151950 | A1 | 10/2013 | | |
| WO | WO2013151960 | * | 10/2013 | ............... | B22C 1/00 |
| WO | 2013170005 | A1 | 11/2013 | | |
| WO | 2015/057943 | A2 | 4/2015 | | |
| WO | 2017083476 | A1 | 5/2017 | | |
| WO | 2017192347 | A1 | 11/2017 | | |
| WO | 2019/046243 | A2 | 3/2019 | | |

OTHER PUBLICATIONS

Bourne "Prophylactic Use of Antibiotic Bone Cement an Emerging Standard- in the Affirmative" 2004, J. of Arthroplasty 19(4)(S1):69-72.
Bragdon et al. "A New Pin-on-disk Wear Testing Method for Simulating Wear of Polyethylene on Cobalt-chrome Alloy in Total Hip Arthroplasty" 2001, J. Arthroplasty 16:658-665.
Darouiche "Device-Associated Infections: A Macroproblem that Starts with Microadherence" 2001, Clinical Infectious Diseases 33:1567-1572.
DeKok et al. "Reactivity of Peptides in Maillard Reactin" in Symposium on Thermally Generated Flavors: Maillard, Microwave, and Extrusion Processes 1994 Ed. American Chemical Society, Washington, DC pp. 158-179.
Eichner et al. "Detection of Amadori Compounds in Heated Foods" in Symposium on Thermally Generated Flavors: Maillard, Microwave, and Extrusion Process 1994 Ed., American Chemical Society, Washington, DC pp. 42-54.
Gogja et al. "Local Antibiotic Therapy in Osteomyelitis" 2009, Semin. Plast. Surg. 23(2):100-107.
International Search Report and Written Opinion for PCT/US2016/061256 dated Feb. 9, 2017.
International Search Report and Written Opinion for PCT/US2017/029789 dated Jul. 19, 2017.
International Search Report and Written Opinion for PCT/US2019/060904 dated Jan. 28, 2002.
Maillard "Action Des Acides Amines Sur Les Sucres: Formation Des Melanoidines Par Voie Methodique" 1912, C. R. Hebd. Seances Acad. Sci. 154(1912):66-68 (abstract only).
Mortin et al. "Rapid Bactericidal Activity of Daptomycin Against Methicillin-Resistant and Methicillin-Susceptible *Staphylococcus aureus* Peritonitis in Mice as Measured with Bioluminescent Bacteria" 2007, Antimicrob. Agents Chemotherapy 51(5):1787-1794.
Oral et al. "A Surface Crosslinked UHMWPE Stabilized by Vitamin E With Low Wear and High Fatigue Strength" Sep. 2010, Biomaterials 31(27):7051-7060.
Spellberg et al. "Systemic Antibiotic Therapy for Chronic Osteomyelitis in Adults" 2012, Clin. Infect. Dis. 54(3):393-407.
Stevens et al. "An Articulating Antibiotic Spacer Used for Infected Total Knee Arthroplasty: a Comparative in vitro Elution Study of Simplex and Palacos Bone Cements" 2005 J. Orthop. Res. Off Publ. Orthop. Res. Soc. 23(1):27-33.
Suhardi et al. "A Fully Functional Drug-eluting Joint Implant" Jun. 13, 2017, Nature Biomedical Engineering 1:1-11.
Van de Belt et al. "Surface Roughness, Porosity and Wettability of Gentamicin-loaded Bone Cements and Their Antibiotic Release" 2000, Biomaterials 21:1981-1987.
Van de Belt et al. "Infection of Orthopedic Implants and the Use of Antibiotic-Loaded Bone Cements: a Review" 2001, Acta Orthopaedica Scandinavica 72(6):557-571.
International Search Report and Written Opinion for PCT/US2020/024497 dated Jul. 2, 2020.
Atkinson et al., Materials for internal prostheses: the present position and possible future developments. Biomaterials. Apr. 1980;1(2):89-99.
Chen et al., Photocrosslinking of Polyethylene. I. Photoinitiators, Crosslinking Agent, and Reaction Kinetics. Journal of Polymer Science Part A: Polymer Chemistry Edition. 1989;27(12):4051-4075.
Costa et al., Mechanisms of Crosslinking, Oxidative Degradation and Stabilization of UHMWPE. UHMWPE Biomaterials Handbook, Second Edition. Chapter 21, pp. 309-323, (2009).
Fang et al., Processing and mechanical properties of HA/UHMWPE nanocomposites. Biomaterials. Jul. 2006;27(20):3701-7.
Irganox 1010, Phenolic Primary Antioxidant for Processing and Long-Term Thermal Stabilization, Ciba Specialty Chemicals, Inc. 2 pages, Aug. 1998.
John, Plastics Research, Evaluation of cross-linked UHMWPE with regards to its suitability as implant material for hip joint shells. Manfred H. Wagner. Polymer Technology/Plastics Technical Center, Berlin. 155 pages, Nov. 2003.
Kurtz et al., Vitamin-E Blended UHMWPE Biomaterials. UHMWPE Biomaterials Handbook, Third Edition, Ultra High Molecular Weight Polyethylene in Total Joint Replacement and Medical Devices. pp. 293-306, (2016).
Morshedian et al., Polyethylene Cross-linking by Two-step Silane Method: A Review. Iranian Polymer Journal. 2009; 18(2):103-128.
Muratoglu et al., Gradient crosslinking of UHMWPE using irradiation in molten state for total joint arthroplasty. Biomaterials. Feb. 2002;23(3):717-24.
Oral et al., Peroxide cross-linked UHMWPE blended with vitamin E. J Biomed Mater Res B Appl Biomater. Aug. 2017;105(6):1379-1389.
R.T. Vanderbilt Company Inc., Comprehensive VAROX Peroxide Accelerator Product Guide. www.rtvanderbilt.com, 31 pages, Apr. 18, 2012.
R.T. Vanderbilt Company Inc., Varox DBph Liquid, Peroxide Accelerator, 2,5-dimethyl-2,5-di(t-butylperoxy)hexane. Chemicals Technical Data Sheet. 2 pages, Apr. 18, 2011.
International Search Report and Written Opinion for Application No. PCT/US2010/024935, dated Sep. 27, 2010, 13 pages.
International Search Report and Written Opinion for Application No. PCT/US2013/034887, dated Sep. 26, 2013, 6 pages.
International Search Report and Written Opinion for Application No. PCT/US2014/060865, dated Mar. 13, 2015, 12 pages.
International Search Report and Written Opinion for Application No. PCT/US2018/048256, dated Mar. 13, 2019, 16 pages.
Atici et al., The effect of gentamicin concentration on gentamicin-eluting UHMWPE. ORS Annual Meeting, Poster No. 1745, 1 page, (2019).
Grindy et al., Percolation thresholds of drugs eluting from Ultra-High Molecular Weight Polyethylene. ORS Annual Meeting, Poster No. 1872, 1 page, (2019).
Suhardi et al., A fully functional drug-eluting joint implant. Nature Biomedical Engineering. 2017;1:0080 with supplemental information, 32 pages.
U.S. Appl. No. 13/202,014, filed Oct. 31, 2011, U.S. Pat. No. 8,933,145, Issued.
U.S. Appl. No. 14/584,519, filed Dec. 29, 2014, U.S. Pat. No. 9,731,047, Issued.
U.S. Appl. No. 15/653,977, filed Jul. 19, 2017, 2018-0161480, Abandoned.
U.S. Appl. No. 16/229,400, filed Dec. 21, 2018, U.S. Pat. No. 10,967,100, Issued.
U.S. Appl. No. 17/222,398, filed Apr. 5, 2021, U.S. Pat. No. 11,850,329, Issused.
U.S. Appl. No. 14/389,852, filed Oct. 1, 2014, 2016-0215117, Abandoned.
U.S. Appl. No. 17/703,288, filed Mar. 24, 2022, U.S. Pat. No. 11,970,600, Issued.
U.S. Appl. No. 18/618,523, filed Mar. 27, 2024, 2024-0240005, Published.

* cited by examiner

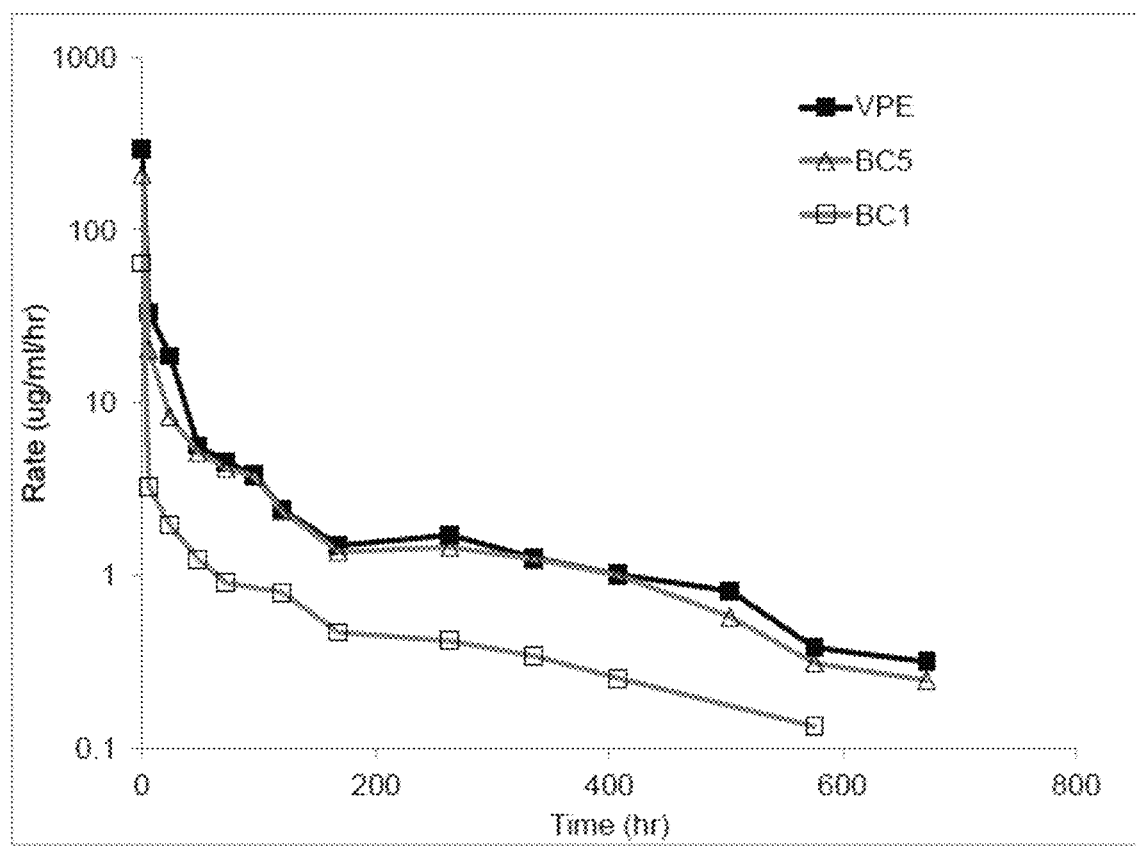
Figure 1. Rate of vancomycin release from vancomycin blended-UHMWPE (VPE), 5 gram vancomycin in 40 gram bone cement (BC5), and 1 gram vancomycin in 40 gram bone cement (BC1).

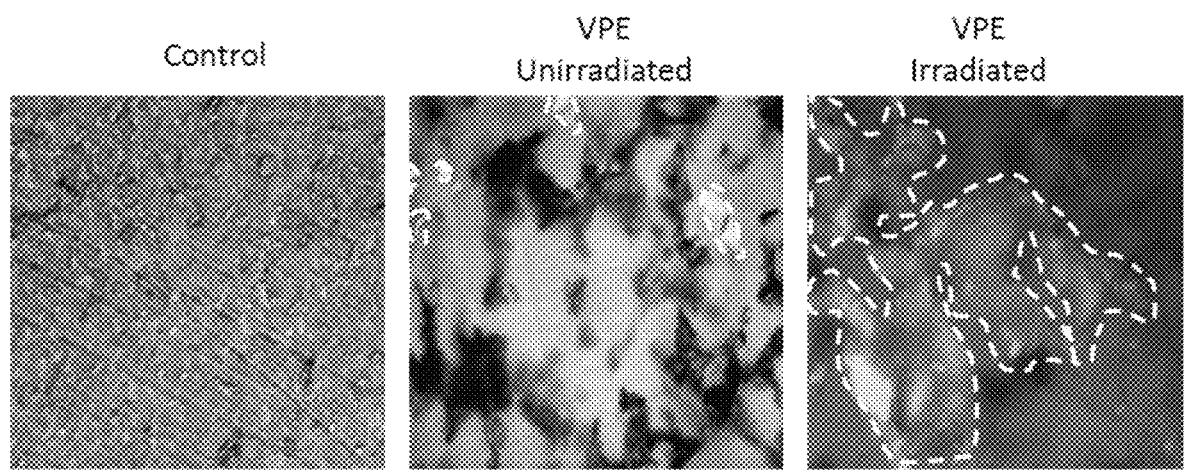
Figure 2. Fluorescent antibody staining for vancomycin on UHMWPE without additives (control), vancomycin-blended UHMWPE in its unirradiated form (VPE unirradiated) or after irradiation at 25-40 kGy (VPE irradiated). Green color indicating vancomycin presence is shown inside the dashed white lines.

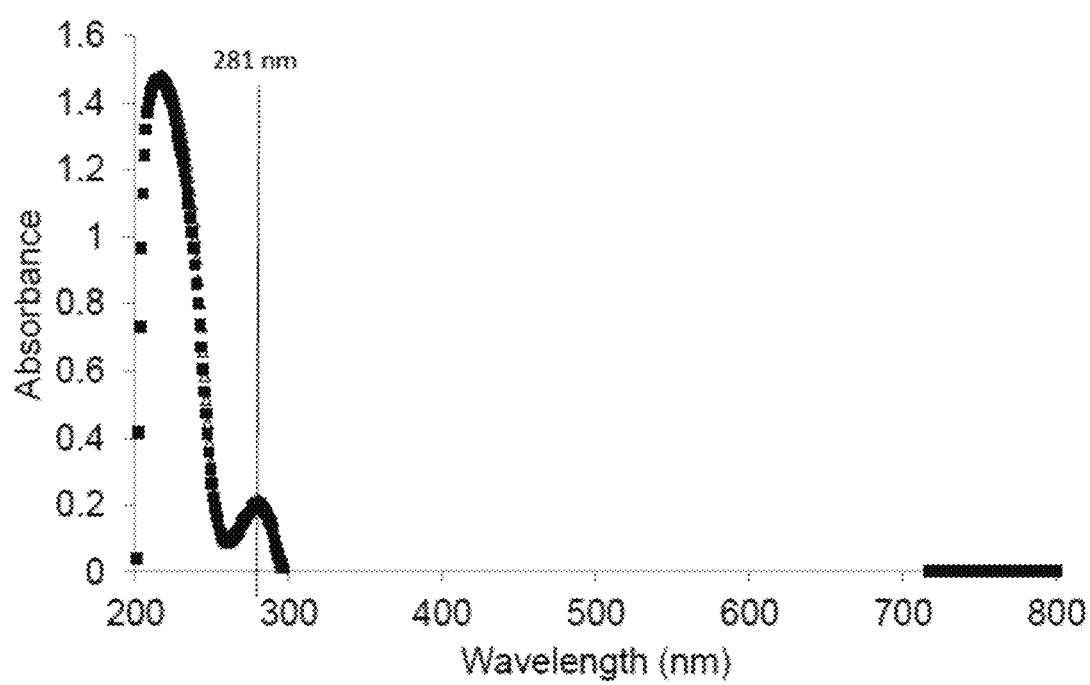
Figure 3. UV-Vis spectra of vancomycin eluted from unirradiated (Δ) and irradiated (■) vancomycin-blended UHMWPE. The main absorbance peak is at 281 nm in both cases.

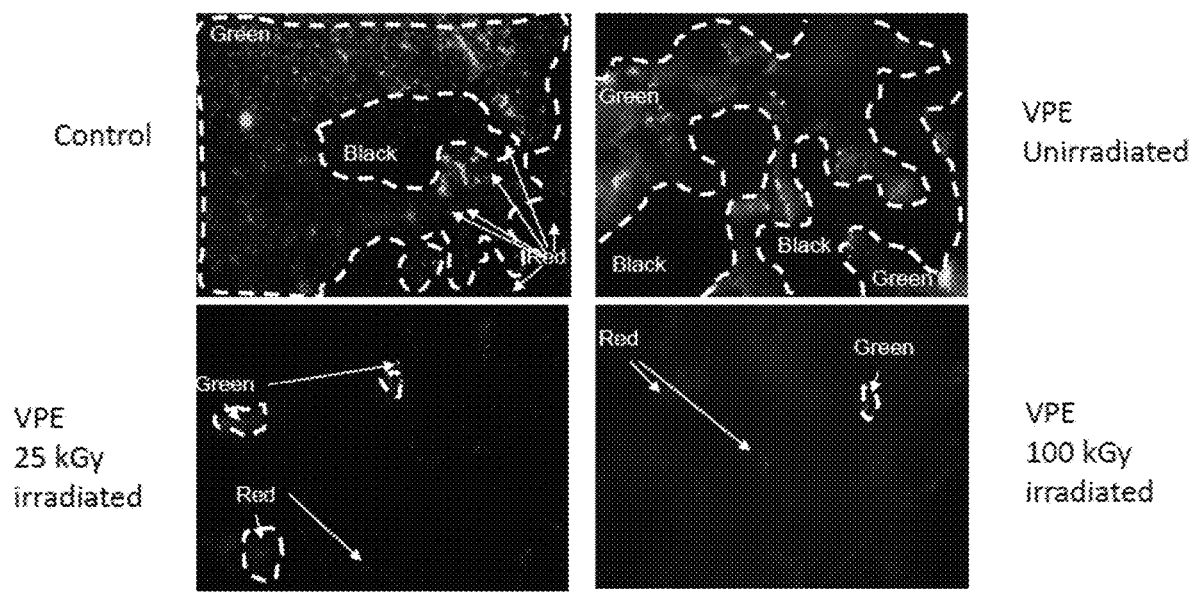

Figure 4. Live-dead staining for bacteria adhered to the surface of UHMWPE without additives (control) and vancomycin-blended UHMWPE in its unirradiated form (VPE unirradiated) or after irradiation at 25 and 100kGy (VPE irradiated). Green color indicates live bacteria, red color indicates dead bacteria; the colors are shown in regions demarcated by dashed lines and single spots are shown by arrows.

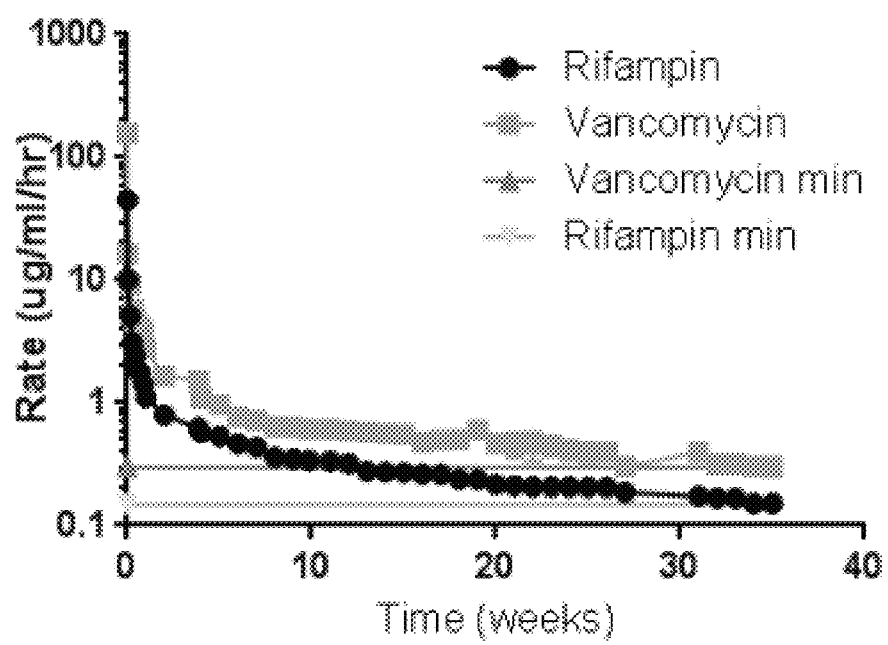
Figure 5. Drug elution into PBS at 37°C from 3.3 wt% rifampin and 6.7 wt% vancomycin-blended UHMWPE (1 mm layer on 4 mm UHMWPE without additives).

Figure 6. The layered construct model simulating a peri-prosthetic infection at the implant-bone interface.

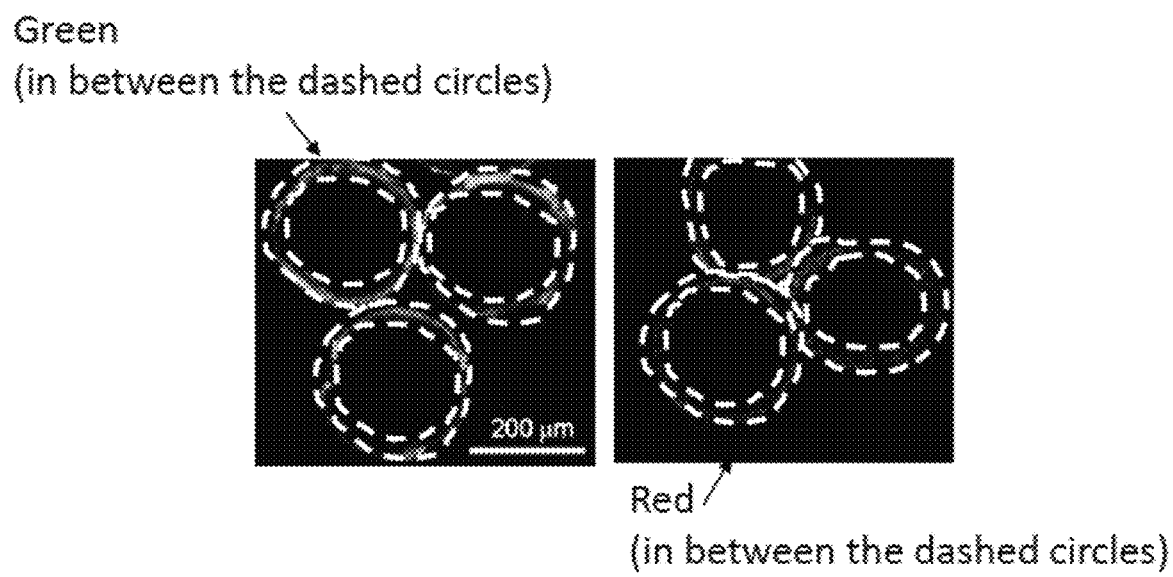

Figure 7. Two-photon fluorescence of live and dead bacteria on the beaded titanium surfaces used in conjunction with UHMWPE without additives (control) and rifampin and vancomycin-blended UHMWPE (RVPE). Green color indicates live bacterial, red color indicates dead bacteria; the colors are shown in regions demarcated by dashed lines and single spots are shown by arrows.

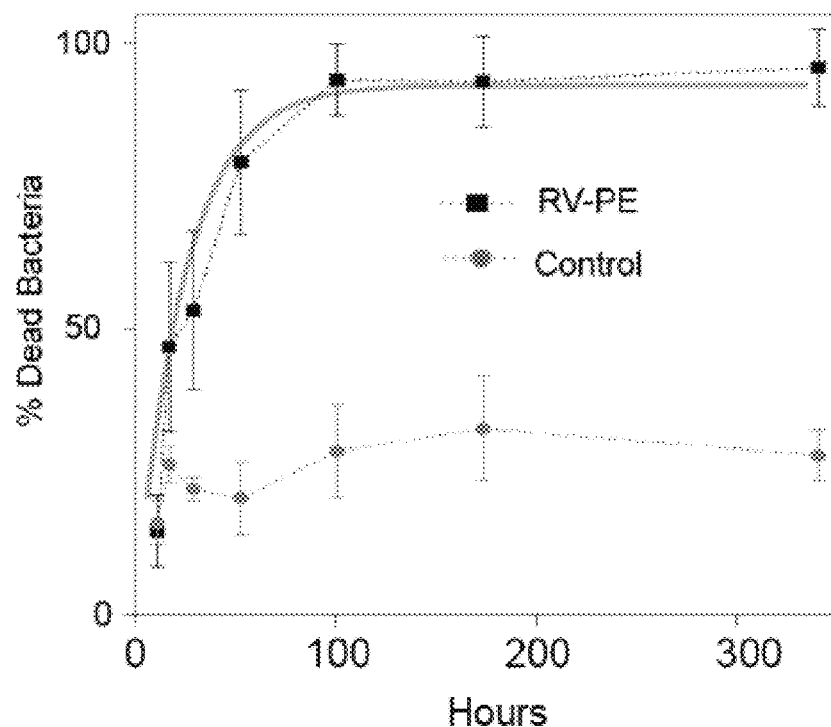
Figure 8. Percent red fluorescence (indicator of percentage of dead bacteria) vs time exposed to treatment as monitored by two photon fluorescence microscopy. RV-PE: Rifampin and vancomycin-blended UHMWPE. Negative control was prepared by exposing the bacteria cultured for 48 hours to 70% ethanol.

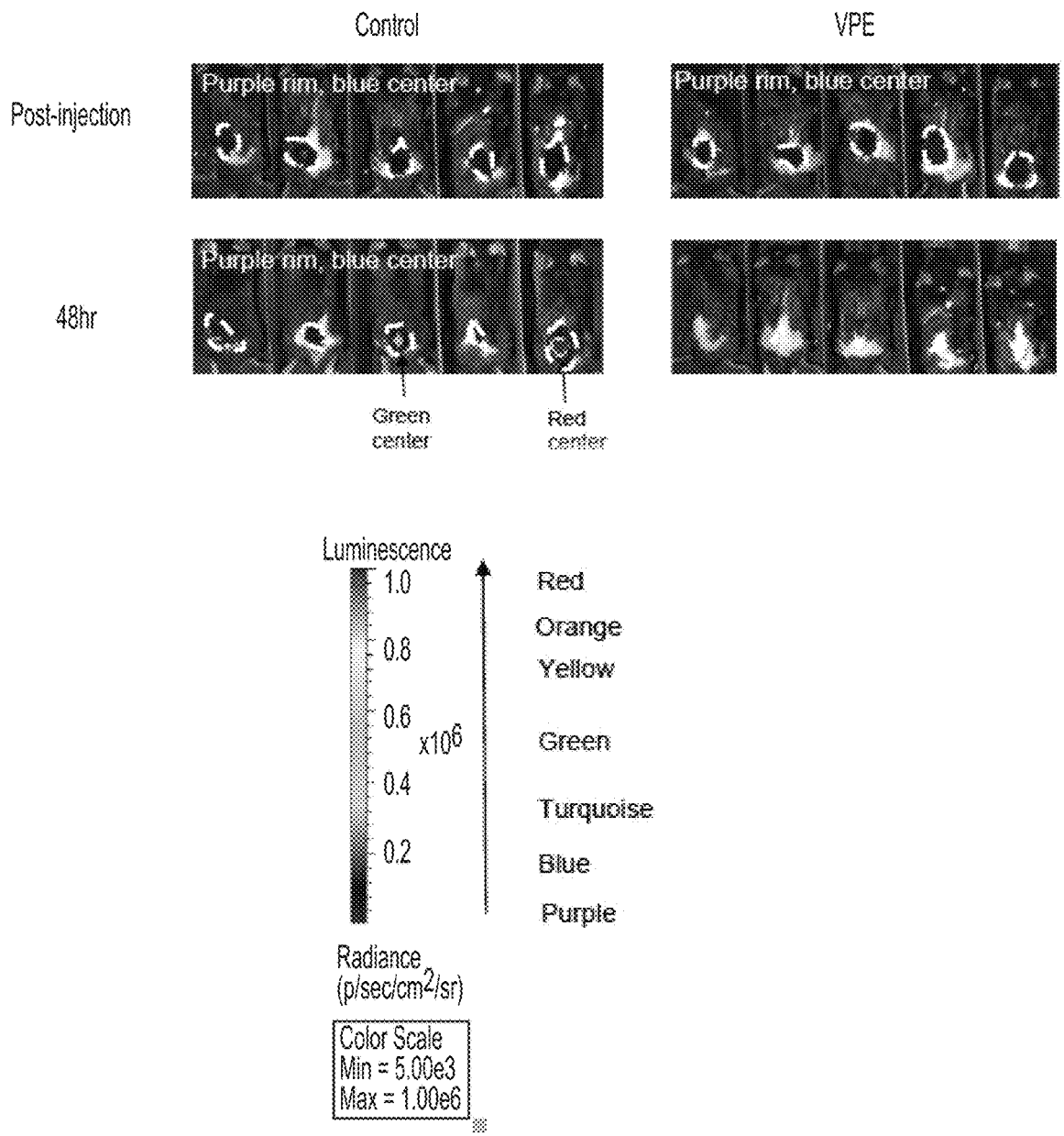
Figure 9. Bioluminescence observed in mice infected with bioluminescent S. aureus (Xen 29) in dorsal subcutaneous pockets while being treated with UHMWPE containing no additives (control) and vancomycin (VPE). Regions where bacteria was measureable by bioluminescence were demarcated by a dashed white line and the intensity was indicated by the coloring.

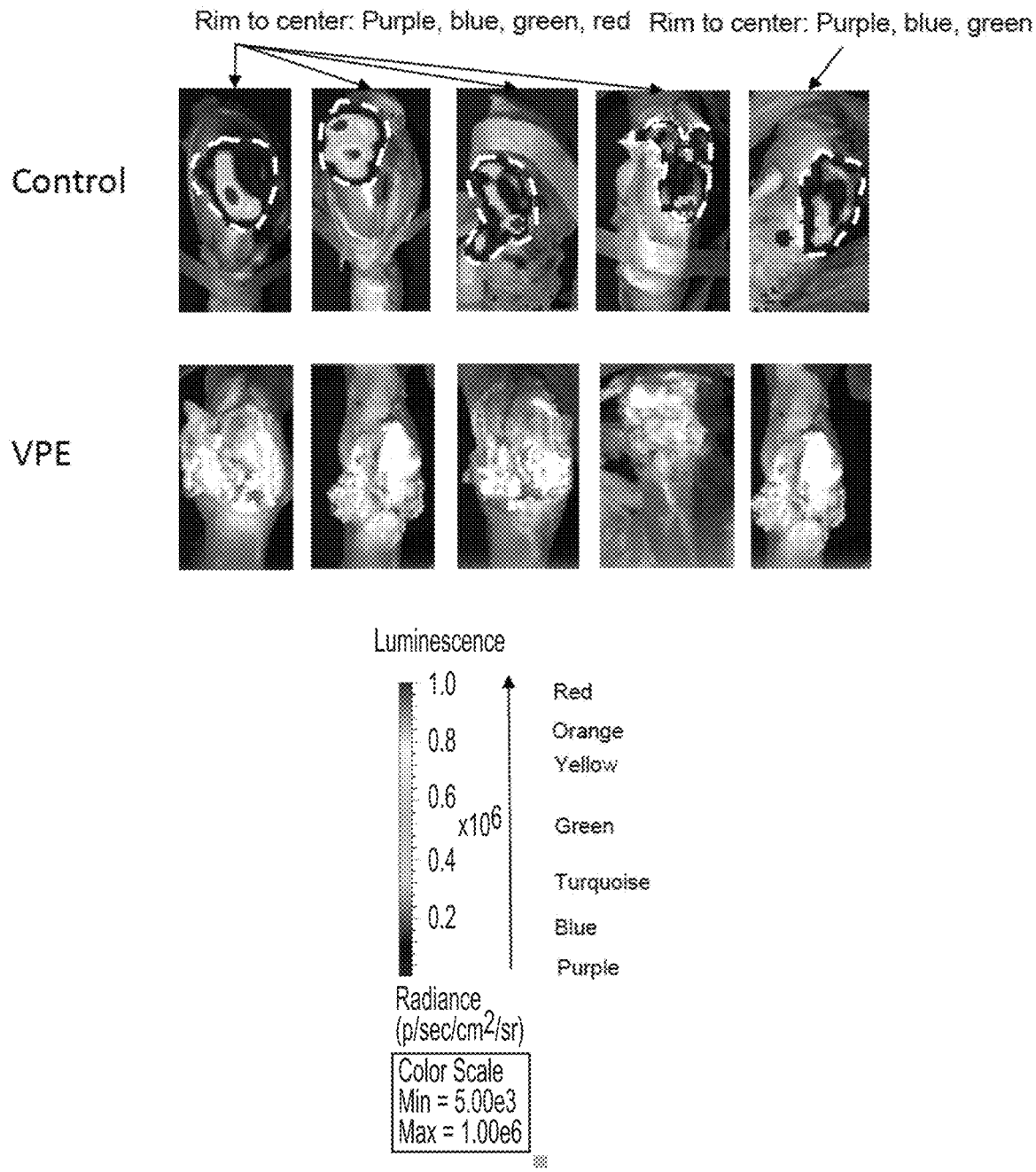

Figure 10. Bioluminescence of the dissected rabbit knee post mortem (day 21) after being treated with UHMWPE without additives (control) and vancomycin-blended UHMWPE (VPE). Color bar indicates the total amount of photon entering the camera, which positively correleates with number of bacteria. Regions where bacteria was measurable by bioluminescence were demarcated by a dashed white line and the intensity was indicated by the coloring.

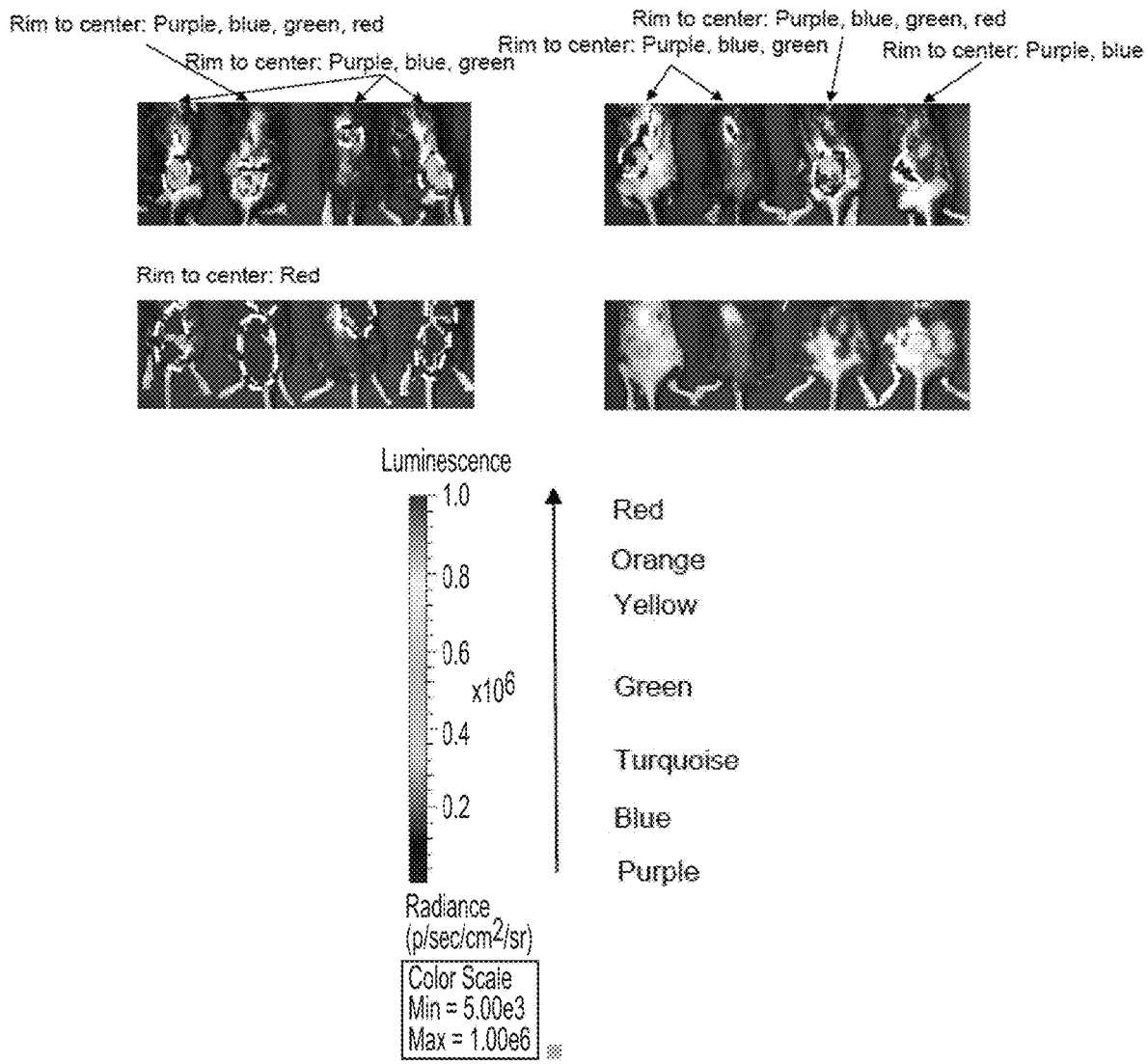

Figure 11. Bioluminescence of the mice after being injected with bacterial and treated with UHMWPE without additives (control) and rifampin and vancomycin-blended UHMWPE (RVPE). Color bar indicates the total amount of photon entering the camera, which positively correlates with number of bacteria. Regions where bacteria was measurable by bioluminescence were demarcated by a dashed white line and the intensity was indicated by the coloring.

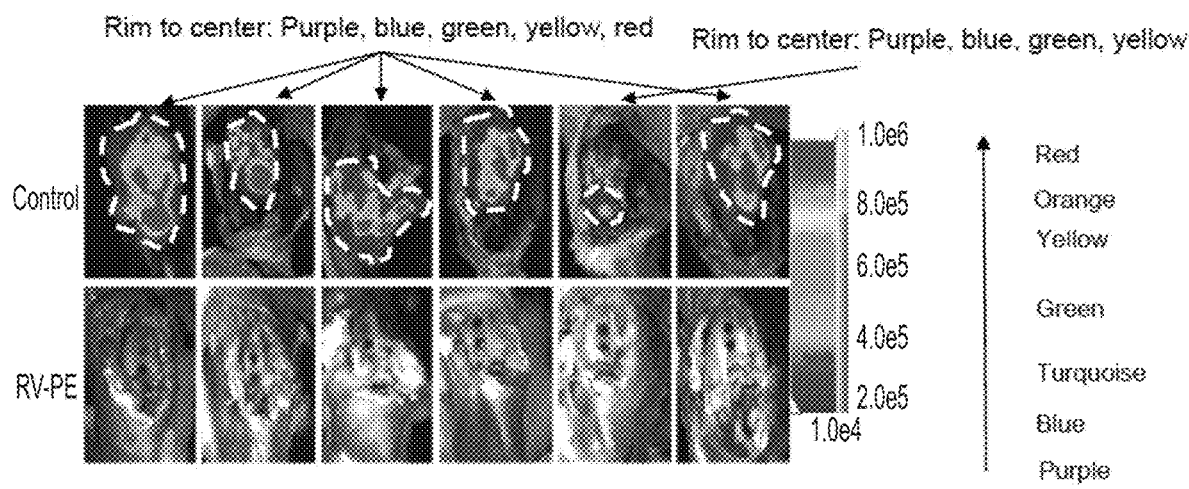

Figure 12. Bioluminescence of the dissected rabbit knee post mortem (day 21) after being treated with UHMWPE without additives (control) and rifampin and vancomycin-blended UHMWPE (RVPE). Color bar indicates the total amount of photon entering the camera, which positively correlated with number of bacteria. Regions where bacteria was measurable by bioluminescence were demarcated by a dashed white line and the intensity was indicated by the coloring.

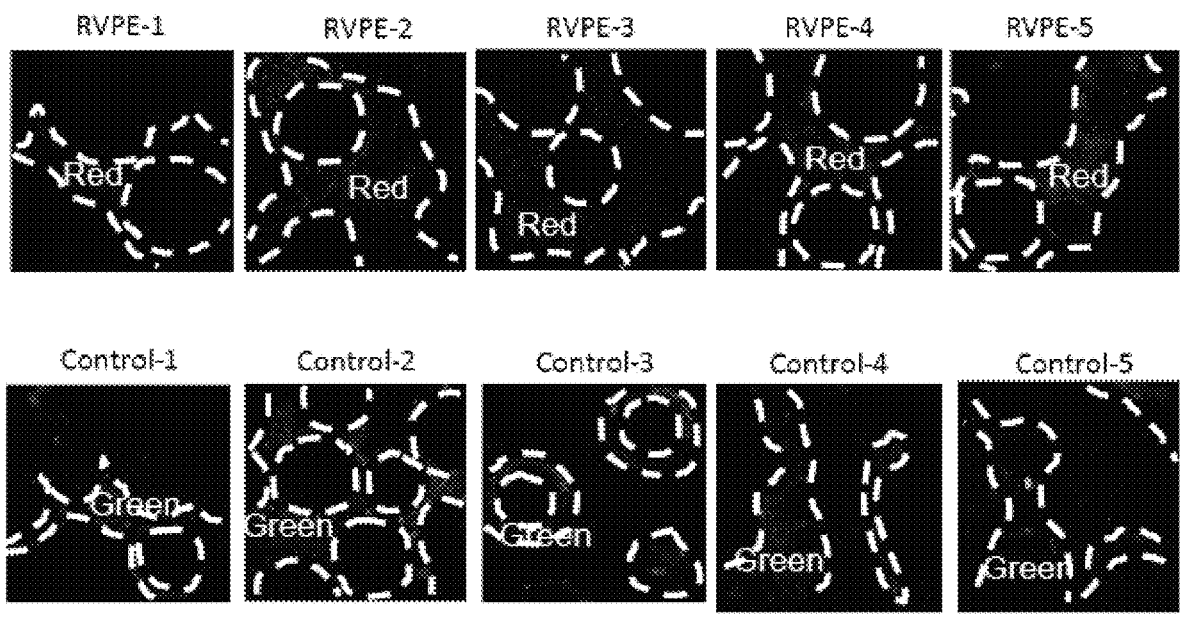

Figure 13. Two photon fluorescence of live and dead bacteria on beaded titanium surfaces of the titanium rods retrieved from rabbits where treatment was in conjunction with a UHMWPE without additives (control) or a rifampin and vancomycin-blended UHMWPE. Green color indicates live bacteria, red color indicates dead bacteria. Regions where bacteria was measurable by fluoroscence were demarcated by a dashed white line and the coloring was indicated.

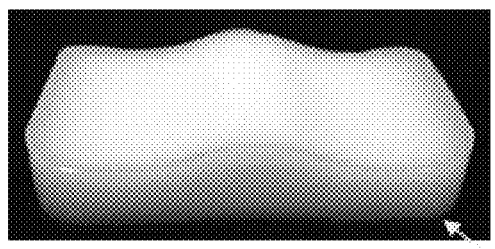
1 mm layer of rifampin and vancomycin-blended UHMWPE (red)
Figure 14. Consolidated, layered, therapeutic UHMWPE implant (tibial insert). Therapeutic agent-blended layer is on the bottom.

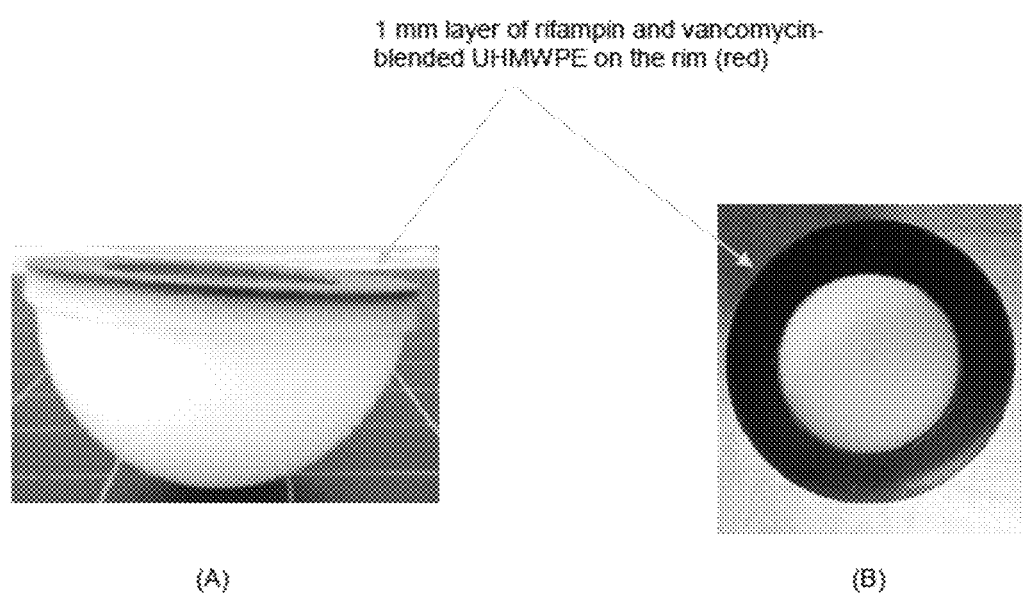
Figure 15. Consolidated, layered, therapeutic UHMWPE implant (acetabular cup. Side view (A) and top view (B)).

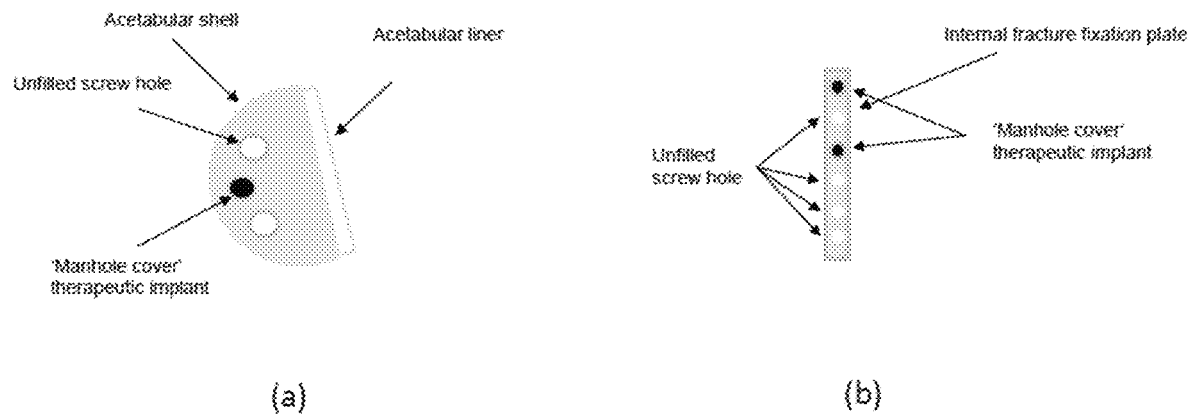
Figure 16. Schematic examples of a therapeutic medical implant used in the form of a 'manhole cover' in conjunction with an acetabular shell in total hip replacement (a) and with an internal fixation plate in bony fracture fixation (b).

METHODS OF MAKING THERAPEUTIC POLYMERIC MATERIAL

CROSS REFERENCE TO RELATED APPLICATIONS

The present application is a 371 of International App. No. PCT/US2016/061256 filed Nov. 10, 2016, which claims the benefit of priority to U.S. Provisional App. No. 62/254,409 filed Nov. 12, 2015. The entire contents of the above-identified applications are hereby incorporated by reference.

FIELD OF THE INVENTION

The present invention relates to methods for making therapeutic polymeric materials. Methods of making medical implants containing additives and polymers and materials used therewith also are provided. Methods of spatially controlling additive concentrations and release as well as polymeric material morphology are also provided.

BACKGROUND OF THE INVENTION

Medical device associated infections are common complication that causes significant mortality and morbidity in patients. In the United States, it is estimated that annually 3 to 9 million and 150,000 to 400,000 of bladder catheter and central venous catheter are infected respectively (Darouiche, R O. Device-Associated Infections: A Macroproblem that Starts with Microadherence. *Clinical Infectious Diseases*, 2001, 33:1567-1572). In the orthopedic field, 100,000 to 200,000 fracture fixation devices, and 6,000 to 18,000 joint prostheses are infected in U.S. annually.

Current treatment for medical device associated infections in orthopaedic applications, e.g. joint replacements, include removal of the device, debridement of potentially infected tissues surrounding the implants, filling the previously implanted spaces with antibiotic-loaded bone cement and parenteral administration of antibiotics for at least 6-weeks (while the patient is immobilized), and a second surgery for re-implantation with new implants. Alone, parenteral administration of antibiotics is not effective for treating medical device associated infections because the antibiotic penetration to the site of infection depends on the blood flow to the infected site. Areas with relatively low blood flow (e.g. bone, cartilage, immediate area surrounding medical implants) have low local concentration of antibiotics compared to areas with relatively high blood flow (e.g. liver, kidney), which have high concentration of antibiotics. For example, only 7-15% of intravenous cefazolin, 5-20% of intravenous vancomycin, and 5-19% of intravenous ceftriaxone penetrate bone (Spellberg B, Lipsky B A. Systemic Antibiotic Therapy for Chronic Osteomyelitis in Adults. *Clin Infect Dis,* 2012, 54(3):393-407). Thus, infections of tissues with low blood flow such as cartilage and bone are difficult and there is a need to improve the local concentration of antibiotics for treatment of infection of these tissues.

To address this problem, the available drug-eluting polymeric materials are bone cements; several drug eluting bone cements (PMMA-based in situ curing polymers) are available and in clinical use for the local delivery of antibiotics. For example, gentamicin containing bone cement that contains 1.0 gram gentamicin in a 40 g unit is commercially available under the trade name SmartSet® GHV Gentamicin, DePuy® CMW 2 Gentamicin, and Zimmer® Palacos R+G. Gentamicin containing bone cements can be used in total joint replacement both as prophylaxis or as treatment (Bourne R B. Prophylactic use of antibiotic bone cement an emerging standard—in the affirmative. *J of Arthroplasty,* 2004, 19(4), Suppl 1, 69-72). The gentamicin released from these bone cements reaches 10 $\mu g/cm^2/h$ but decreases significantly to 0.1-1 $\mu g/cm^2/h$ by 24 hr and below 0.1 $\mu g/cm^2/hr$ by 1 week (Van de Belt H, Neut D, Uges D R A, Schenk W, van Horn J R, van der Mei H C, Busscher H J. Surface roughness, porosity and wettability of gentamicin-loaded bone cements and their antibiotic release. *Biomaterials,* 2000, 21:1981-1987). Because the amount of antibiotic eluted by the commercially available bone cement is very low after 24 hr, often at levels below the minimum inhibitory concentration or MIC associated with the microorganisms causing infections, the commercially available antibiotic cements are ineffective as a lone treatment for infection (Gogja J S, Meehan J P, Di Cesare, P, Jamali A A. Local Antibiotic Therapy in Osteomyelitis. *Semin Plast Surg,* 2009, 23(2):100-107). Clinical efficacy of antibiotic eluting bone cement as prophylaxis is inconclusive.

The present invention relates to incorporating therapeutic agents in polymeric materials, for example antibiotics into polymeric total joint implants, for delivery of therapeutic agents into the surrounding mediums.

SUMMARY OF THE INVENTION

The present invention relates to methods of making therapeutic medical implants with optimum properties for clinical performance. For example, in total joint replacement bearing surfaces made out of UHMWPE as polymeric material, the addition of additives such as therapeutic agents can increase the wear rate of the bearing surfaces and/or decrease the mechanical strength of the implants. These shortcomings can be overcome by novel strategies such as including therapeutic polymeric material on portions of the implant which would not interfere with their wear properties. Alternatively, the invention also relates to methods of making layered constructs of polymeric material so that mechanical properties are not compromised. Alternatively, the invention relates to methods of making medical implants with non-homogenous distribution of therapeutic agents.

Wear resistance of total joint implants can be measured by pin-on-disc wear testers or joint simulators under clinically relevant loads (stresses) and multidirectional, crossing motion to produce clinically relevant wear mechanisms. In this context, the wear rate is described under these conditions.

Various teachings and embodiments of the invention are described below. These descriptions are meant to be illustrative and permissive, and do not restrict the invention in any way or manner.

In an embodiment, the invention provides a method of making a consolidated polymeric material comprising: (i) providing a polymeric material; (ii) blending the polymeric material with therapeutic agent(s); (iii) layering the therapeutic agent-blended polymeric material with polymeric material that may not contain therapeutic agent(s); (iv) consolidating the layered polymeric material; thereby obtaining a consolidated polymeric material.

In an embodiment, the invention provides a method of making a consolidated polymeric material comprising: (i) providing a polymeric material; (ii) diffusing therapeutic agent(s) into the polymeric material; (iii) layering the therapeutic agent-diffused polymeric material with polymeric material (s); (iv) consolidating the layered polymeric material; thereby obtaining a consolidated polymeric material.

In an embodiment, the invention provides a method of making a consolidated polymeric material comprising: (i) providing a polymeric material; (ii) blending the polymeric material with antibiotic(s); (iii) layering the antibiotic-blended polymeric material with polymeric material that does not contain antibiotic(s); (iv) consolidating the layered polymeric material; thereby obtaining a consolidated polymeric material.

In an embodiment, the invention provides a method of making a consolidated polymeric material comprising: (i) providing a polymeric material; (ii) blending the polymeric material with antibiotic(s) and other additive(s); (iii) layering the additive-blended polymeric material with polymeric material that does not contain antibiotic(s); (iv) consolidating the layered polymeric material; thereby obtaining a consolidated polymeric material.

In an embodiment, the invention provides a method of making a consolidated polymeric material comprising: (i) providing a polymeric material; (ii) blending the polymeric material with vancomycin and vitamin E; (iii) layering the vitamin E and vancomycin-blended polymeric material with polymeric material that does not contain antibiotic(s); (iv) consolidating the layered polymeric material; thereby obtaining a consolidated polymeric material.

In an embodiment, the invention provides a method of making a consolidated polymeric material comprising: (i) providing a polymeric material; (ii) blending the polymeric material with vancomycin, rifampin and vitamin E; (iii) layering the vitamin E and vancomycin and rifampin-blended polymeric material with polymeric material that does not contain antibiotic(s); (iv) consolidating the layered polymeric material; thereby obtaining a consolidated polymeric material.

In an embodiment, the invention provides a method of making a consolidated polymeric material comprising: (i) providing a polymeric material; (ii) blending the polymeric material with vancomycin; (iii) layering the vancomycin-blended polymeric material with polymeric material that does not contain antibiotic(s); (iv) consolidating the layered polymeric material; thereby obtaining a consolidated polymeric material.

In an embodiment, the invention provides a method of making a consolidated polymeric material comprising: (i) providing a polymeric material; (ii) blending the polymeric material with rifampin and vancomycin; (iii) layering the rifampin and vancomycin-blended polymeric material with polymeric material that does not contain antibiotic(s); (iv) consolidating the layered polymeric material; thereby obtaining a consolidated polymeric material.

In any embodiments, the concentration of therapeutic agents in the polymeric material can be 0.001 wt % to 50 wt %, or any value thereabout or therebetween, preferably above 5 wt % to 25 wt %, more preferably from 6 wt % to 10 wt %, or about 8 wt %. When multiple therapeutic agents are used, their concentrations can be the same or different. The concentration of each therapeutic agent can be 0.001 wt % to 50 wt %, or any value thereabout or therebetween, preferably about 2 wt % to 8 wt %, more preferably from 2 wt % to 6 wt %. The use of multiple therapeutic agents can be synergistic against infectious agents; for example, the addition of rifampin to vancomycin in the polymeric material can increase the effectiveness of vancomycin, thus making the therapeutic polymeric material more effective than if the polymeric material contained the antibiotics separately at the designated concentrations.

In an embodiment, the invention provides a method of making a medical implant comprising: (i) providing a polymeric material; (ii) blending the polymeric material with therapeutic agent(s); (iii) layering the therapeutic agent-blended polymeric material with polymeric material; (iv) consolidating the layered polymeric material; thereby forming an implant.

When layers of polymeric material blended with therapeutic agents are used, the layers may contain the same or different agents or different chemical forms of the same therapeutic agent, and in the same or varying concentrations. For example, vancomycin may be present as a hydrochloride or a free base. In another embodiment, one layer may contain a single agent such as vancomycin and another may contain multiple agents such as vancomycin and rifampin. Any number of layers containing therapeutic agents and layers not containing therapeutic agents may be used.

In an embodiment, the invention provides a method of making a medical implant comprising: (i) providing a polymeric material; (ii) blending the polymeric material with therapeutic agent(s); (iii) layering the therapeutic agent-blended polymeric material with polymeric material; (iv) consolidating the layered polymeric material; thereby forming an implant preform; (v) machining the medical implant preform; thereby obtaining a medical implant.

In an embodiment, the invention provides a method of making a hybrid, consolidated material comprising: (i) providing a polymeric material; (ii) blending the polymeric material with therapeutic agent(s); (iii) providing a polymeric material without therapeutic agent(s); (iv) providing a third surface; (v) layering the therapeutic agent-blended polymeric material, the polymeric material and the third surface; (vi) consolidating the layered polymeric material; thereby obtaining a hybrid, consolidated material. In this embodiment, the third surface provided can be a metal or a porous metal. Or it can be a metal which has porous surfaces and non-porous surfaces and the contact with the polymeric material layers can be on the porous or non-porous surfaces. By consolidation, the interface between the polymeric material layers and the third surface is strengthened, obtaining a strong, interlocked, hybrid structure. In prior art such constructs are known and referred to as monoblock implants. For example, a monoblock acetabular liner or a tibial insert used in total joint replacement. The monoblock implants do not have a mechanical locking mechanism that is activated by the surgeon in the operating room, for example, to fix the UHMWPE total joint implant components inside a metal backing.

In an embodiment, the invention provides a method of making a hybrid, medical implant comprising: (i) providing a polymeric material; (ii) blending the polymeric material with therapeutic agent(s); (iii) providing a polymeric material without therapeutic agent(s); (iv) providing a third surface; (v) layering the therapeutic agent-blended polymeric material, the polymeric material and the third surface; (vi) consolidating the layered polymeric material; thereby obtaining a hybrid, medical implant. In this embodiment, the third surface provided can be a metal or a porous metal. Or it can be a metal which has porous surfaces and non-porous surfaces and the contact with the polymeric material layers can be on the porous or non-porous surfaces. By consolidation, the interface between the polymeric material layers and the third surface is strengthened, obtaining a strong, interlocked, hybrid structure.

In an embodiment, the invention provides a method of making a therapeutic medical implant comprising: (i) providing a polymeric material; (ii) blending the polymeric material with therapeutic agent(s); (iii) providing a polymeric material without therapeutic agent(s); (iv) layering the first layer of therapeutic agent-blended polymeric material, the second layer of polymeric material and the third layer of therapeutic agent-blended polymeric material; (vi) consolidating the layered polymeric material; thereby obtaining a therapeutic medical implant. In this embodiment, the polymeric material in the first, second and third layers can be the same or different or a mixture containing different polymers. In this embodiment, the concentration and type of the therapeutic agent(s) in the first and third layers of blended polymeric material can be the same or different. The medical implant can be implanted abutting another surface such as a porous or non-porous metal.

In an embodiment, the invention provides a method of making a consolidated polymeric material comprising: (i) providing a polymeric material; (ii) blending the polymeric material with therapeutic agent(s); (iii) providing a polymeric material without therapeutic agent(s); (iv) layering the first layer of therapeutic agent-blended polymeric material, the second layer of polymeric material and the third layer of therapeutic agent-blended polymeric material; (vi) consolidating the layered polymeric material. In this embodiment, the polymeric material in the first, second and third layers can be the same or different or a mixture containing different polymers. In this embodiment, the concentration and type of the therapeutic agent(s) in the first and third layers of blended polymeric material can be the same or different.

In an embodiment, the invention provides a method of making a hybrid, interlocked medical implant comprising: (i) providing a polymeric material; (ii) blending the polymeric material with therapeutic agent(s); (iii) providing a polymeric material without therapeutic agent(s); (iv) providing a surface; (v) layering the first layer of therapeutic agent-blended polymeric material, the second layer of polymeric material and the third layer of therapeutic agent-blended polymeric material and the surface provided as the fourth layer; (vi) consolidating the layered polymeric material and the surface; thereby obtaining a hybrid, interlocked medical implant. In this embodiment, the surface used as the fourth layer can be a metal or a porous metal. This also can be a metal which has porous surfaces and non-porous surfaces and the contact with the polymeric material layers can be on the porous or non-porous surfaces. By consolidation, the interface between the polymeric material layers and the third surface is strengthened, obtaining a strong, interlocked, hybrid structure.

In any of the embodiments, as desired, consolidation can be done by "direct compression molding" to obtain a near-net shape solid form that can be used directly as an implant or with small amounts of manipulation such as machining. In some embodiments, compression molding can be done to obtain an implant preform; that is, a slightly oversized solid form of an implant, which can then be machined with the appropriate precision into an implant.

In any of the embodiments, as desired, an implant is packaged and sterilized.

In an embodiment, the invention provides a method of making a cross-linked therapeutic medical implant comprising: (i) providing a polymeric material; (ii) blending the polymeric material with therapeutic agent(s); (iii) layering the therapeutic agent-blended polymeric material with polymeric material; (iv) consolidating the layered polymeric material; thereby obtaining a consolidated, therapeutic polymeric material; (v) machining the consolidated, therapeutic polymeric material; thereby obtaining a therapeutic medical implant; (vi) irradiating the therapeutic medical implant; thereby obtaining a cross-linked therapeutic medical implant. In embodiments where irradiation or cross-linking is described, the regions or layers of the polymeric material, where the therapeutic agents are located, can coincide with crosslinked regions or are different from the crosslinked regions. Cross-linking of different regions can be done by such methods as spatially controlling radiation energy absorbed by regions of the polymeric material, or by having different concentration of crosslinking or anticrosslinking agents. Controlling radiation exposure by using shields or changing the energy of the radiation or selectively irradiating part of a medical device are described in U.S. Pat. No. 7,381,752 (Muratoglu).

In an embodiment, the invention provides a method of making a cross-linked therapeutic medical implant comprising: (i) providing a polymeric material, (ii) blending the polymeric material with antibiotic(s); (iii) layering the antibiotic-blended polymeric material with polymeric material that does not contain antibiotic(s); (iv) consolidating the layered polymeric material; thereby obtaining a consolidated, therapeutic polymeric material; (v) machining the consolidated, therapeutic polymeric material; thereby obtaining a therapeutic medical implant; (vi) irradiating the therapeutic medical implant; thereby obtaining a cross-linked therapeutic medical implant.

In an embodiment, the invention provides a method of making a cross-linked therapeutic medical implant comprising: (i) providing a polymeric material, (ii) blending the polymeric material with vancomycin and rifampin; (iii) layering the rifampin and vancomycin-blended polymeric material with polymeric material that does not contain antibiotic(s); (iv) consolidating the layered polymeric material; thereby obtaining a consolidated, therapeutic polymeric material; (v) machining the consolidated, therapeutic polymeric material; thereby obtaining a therapeutic medical implant; (vi) irradiating the therapeutic medical implant; thereby obtaining a cross-linked therapeutic medical implant.

In an embodiment, the invention provides a method of making a sterile therapeutic medical implant comprising: (i) providing a polymeric material, (ii) blending the polymeric material with therapeutic agent(s); (iii) layering the therapeutic agent-blended polymeric material with polymeric material; (iv) consolidating the layered polymeric material; thereby obtaining a consolidated, therapeutic polymeric material; (v) machining the consolidated, therapeutic polymeric material; thereby obtaining a therapeutic medical implant; (vi) packaging the therapeutic medical implant; (vii) sterilizing the therapeutic medical implant; thereby obtaining a sterile therapeutic medical implant.

In an embodiment, the invention provides a method of making a cross-linked, consolidated, therapeutic polymeric material comprising: (i) providing a polymeric material, (ii) blending the polymeric material with therapeutic agent(s); (iii) providing a second polymeric material; (iv) blending the second polymeric material with a cross-linking agent; (v) layering the therapeutic agent-blended polymeric material with the cross-linking agent-blended polymeric material; (vi) consolidating the layered polymeric material; thereby obtaining a consolidated, cross-linked, therapeutic polymeric material.

In an embodiment, the invention provides a method of making a cross-linked therapeutic medical implant comprising: (i) providing a polymeric material, (ii) blending the polymeric material with therapeutic agent(s); (iii) providing a second polymeric material; (iv) blending the second polymeric material with a cross-linking agent; (v) layering the therapeutic agent-blended polymeric material with the cross-linking agent-blended polymeric material; (vi) consolidating the layered polymeric material; thereby obtaining a consolidated, therapeutic polymeric material; (vii) machining the consolidated, therapeutic polymeric material; thereby obtaining a therapeutic medical implant.

In an embodiment, the invention provides a method of making a sterile, cross-linked therapeutic medical implant comprising: (i) providing a polymeric material, (ii) blending the polymeric material with therapeutic agent(s); (iii) providing a second polymeric material; (iv) blending the second polymeric material with a cross-linking agent; (v) layering the therapeutic agent-blended polymeric material with the cross-linking agent-blended polymeric material; (vi) consolidating the layered polymeric material; thereby obtaining a consolidated, therapeutic polymeric material; (vii) machining the consolidated, therapeutic polymeric material; thereby obtaining a therapeutic medical implant; (viii) sterilizing the therapeutic medical implant; thereby obtaining a sterile, crosslinked therapeutic medical implant.

In any of the embodiments, the provided polymeric material can be pre-mixed with other additives such as antioxidant(s). For example, the provided polymeric material can be UHMWPE pre-mixed or pre-blended with 0.2 wt % vitamin E. In any of the embodiments, the polymeric material provided to be blended with therapeutic agent can be pre-mixed or pre-blended with other additives. In any of the embodiments, the polymeric material provided to be blended with therapeutic agent can contain additives at the same or different concentration compared to the polymeric material provided to be used without blending with therapeutic agent(s).

In any of the embodiments, the layering can be done such that only the desired parts of an implant contain the therapeutic agent (FIG. 15, for example). For example, the rim of an acetabular cup can contain therapeutic agent(s), whereas the articular surface on the inside of the cup can be made from polymeric material. Alternatively, the articular surface of a tibial insert or just condylar regions can contain therapeutic agent (FIG. 16, for example). Alternatively, the side surfaces or the backside surface of a tibial insert can contain therapeutic agent. Layering can be done by methods such as spraying of the polymeric material blended with therapeutic agent(s) such that the location of the polymeric material containing therapeutic agent(s) can be controlled.

In any of the embodiments, as desired, the polymeric material or the consolidated polymeric material or medical implants or medical implant preforms can be heated before or after any step. The heating can serve to diffuse components, aid in the mixing of components, or relieve stresses. In some embodiments the polymeric material or the preform or the implant is heated prior to and/or after radiation crosslinking or crosslinking by chemical methods such as peroxides. In some embodiments, the polymeric material is heated before, during or after blending or diffusing with additive(s).

In any of the embodiments, as desired, the therapeutic agents can be incorporated into UHMWPE by diffusion. For example, a therapeutic agent can be contacted with a polymeric material or consolidated polymeric material or a crosslinked consolidated material to diffuse the therapeutic agent into the surface(s) of the polymeric material. The therapeutic agent can be contacted in pure form, in a gas, in solution, in emulsion, slurry, or in a supercritical fluid. In an embodiment, the invention describes a method of making a therapeutic polymeric material comprising: (i) providing a polymeric material, (ii), consolidating the polymeric material; (iii) irradiating the consolidated polymeric material; thereby obtaining a cross-linked consolidated polymeric material; (iv) diffusing therapeutic agent(s) into cross-linked, consolidated polymeric material for a period of time; thereby obtaining a therapeutic polymeric material.

In an embodiment, the invention describes a method of making a therapeutic polymeric material comprising: (i) providing a polymeric material, (ii) diffusing therapeutic agent(s) into polymeric material for a period of time; (iii) consolidating the polymeric material; thereby obtaining a therapeutic polymeric material; (iii) irradiating the therapeutic polymeric material.

In an embodiment, the invention describes a method of making a therapeutic polymeric material comprising: (i) providing a polymeric material, (ii) diffusing therapeutic agent(s) into polymeric material for a period of time; (iii) consolidating the polymeric material; thereby obtaining a therapeutic polymeric material.

In an embodiment, the invention describes a method of making a therapeutic polymeric material comprising: (i) providing a polymeric material, (ii) diffusing therapeutic agent(s) and other additive(s) into polymeric material for a period of time; (iii) consolidating the polymeric material; thereby obtaining a therapeutic polymeric material.

In an embodiment, the invention describes a method of making a therapeutic polymeric material comprising: (i) providing a polymeric material, (ii), consolidating the polymeric material; (iii) irradiating the consolidated polymeric material; thereby obtaining a cross-linked consolidated polymeric material; (iv) covering regions of the consolidated polymeric material; (v) diffusing therapeutic agent(s) into consolidated polymeric material for a period of time; thereby obtaining a therapeutic polymeric material. In this embodiment, only the regions of the consolidated polymeric material that are not covered can be diffused with therapeutic agent(s).

In an embodiment, the invention describes a method of making a therapeutic medical implant comprising: (i) providing a polymeric material, (ii), consolidating the polymeric material; (iii) irradiating the consolidated polymeric material; thereby obtaining a cross-linked consolidated polymeric material; (iv) diffusing therapeutic agent(s) into cross-linked, consolidated polymeric material for a period of time; thereby obtaining a therapeutic polymeric material; (v) machining the therapeutic polymeric material; thereby obtaining a therapeutic medical implant.

In an embodiment, the invention describes a method of making a therapeutic medical implant comprising: (i) providing a polymeric material, (ii) blending the polymeric material with a cross-linking agent; (iii) consolidating the polymeric material; thereby obtaining a cross-linked consolidated polymeric material; (iv) diffusing therapeutic agent(s) into cross-linked, consolidated polymeric material for a period of time; thereby obtaining a therapeutic polymeric material; (v) machining the therapeutic polymeric material; thereby obtaining a therapeutic medical implant.

In an embodiment, the invention describes a method of making a therapeutic medical implant comprising: (i) providing a polymeric material, (ii), consolidating the polymeric material; (iii) irradiating the consolidated polymeric material; thereby obtaining a cross-linked consolidated polymeric material; (iv) machining the cross-linked, consolidated polymeric material; thereby obtaining a cross-linked medical implant preform; (v) diffusing therapeutic agent(s) into cross-linked medical implant preform for a period of time; thereby obtaining a therapeutic medical implant preform; (vi) machining the therapeutic medical implant preform; thereby obtaining a therapeutic medical implant.

In an embodiment, the invention describes a method of making a therapeutic medical implant comprising: (i) providing a polymeric material, (ii) blending the polymeric material with a cross-linking agent; (iii) consolidating the polymeric material; thereby obtaining a cross-linked consolidated polymeric material; (iv) machining the cross-linked, consolidated polymeric material; thereby obtaining a cross-linked medical implant preform; (v) diffusing therapeutic agent(s) into the cross-linked medical implant preform for a period of time; thereby obtaining a therapeutic medical implant preform; (v) machining the therapeutic medical implant preform; thereby obtaining a therapeutic medical implant.

In another embodiment, the third surface for layering and consolidation is a metal piece.

In another embodiment, one or some or all of the metal pieces consolidated with the polymeric material is a porous metal piece that allows bone in-growth when implanted into the human body.

In any of the embodiments, as desired, one or some or all of the metal pieces consolidated with the polymeric material is a non-porous metal piece. In other embodiments, the metal pieces consolidated with the polymeric material have a sandwich structure with porous metal surface layers on either side of continuous metal core layer to minimize or eliminate any passage through the pores of the metal piece from one side to the other side.

In any of the embodiments, as desired, the different layers of polymeric material have different concentrations of the same or different therapeutic agent(s). In certain embodiments, one of the different layers of polymeric material has no added therapeutic agent.

In an embodiment, the consolidated polymeric material is irradiated using ionizing radiation such as gamma, electron-beam, or x-ray to a dose level between about 1 and about 10,000 kGy, or any value thereabout or therebetween, preferably about 25 to about 250 kGy, preferably about 50 to about 150 kGy, preferably about 65 kGy, preferably about 85 kGy, preferably about 100 kGy, or preferably about 120 kGy.

In some embodiments, the medical implants are cleaned before packaging and sterilization.

In an embodiment, the invention provides a method of making antibiotic-eluting, load-bearing polymeric materials, where an antibiotic-eluting polymeric material is made in the shape of a bearing surface, for example, an acetabular liner, and is used in a 'two-stage revision for peri-prosthetic joint infection (PJI)' or a 'single-stage revision for PJI'. In this method, materials are used in conjunction with bone cement/antibiotic-eluting bone cement as a fixation aid.

In an embodiment, the invention provides an antibiotic-eluting polymeric material made by this method is made in the shape of a bearing surface, for example, an acetabular liner, is used instead of the antibiotic eluting bone cement spacer in the two-stage surgery. This antibiotic-eluting liner is load-bearing and therefore, the patients is mobilized in a manner consistent with their daily lives while being treated for infection.

In another embodiment, the invention provides an antibiotic-eluting polymeric material made by this method is made in the shape of a bearing surface, for example, an acetabular liner, and is used in a 'liner exchange'. In this method, instead of going through a two-stage surgery, a patient with a suspected and/or confirmed peri-prosthetic joint infection undergoes a single surgery where only the polymeric bearing surface (for example, acetabular liner) is removed, the joint is debrided, washed thoroughly (lavage) and a new bearing surface is placed. In this method, the new liner is made out of the antibiotic-eluting polymeric materials.

In an embodiment, the invention provides a method of making a therapeutic implant comprising: (a) providing a polymeric material; (b) blending the polymeric material with one or more antibiotic(s); (c) layering the polymeric material blended with polymeric material without antibiotic(s); and (d) consolidating the layered polymeric materials, thereby obtaining a therapeutic implant with antibiotic-rich regions.

In another embodiment, the invention provides a method of making a therapeutic implant comprising: (a) providing a polymeric material; (b) blending the polymeric material with one or more antibiotic(s); (c) layering the polymeric material blended with polymeric material without antibiotic(s); (d) consolidating the layered polymeric materials, thereby obtaining a consolidated polymeric material with antibiotic-rich regions; and (e) machining the consolidated polymeric material with antibiotic-rich regions, thereby obtaining a therapeutic implant.

In an embodiment, the invention provides a method of making an implant comprising: (a) providing a polymeric material; (b) blending the polymeric material with antibiotic(s); (c) layering the antibiotic-blended polymeric material polymeric material without antibiotic(s); (d) consolidating the layered polymeric materials, thereby obtaining an implant with antibiotic-rich regions; and (e) exposing at least parts of the implant to radiation.

In another embodiment, the invention provides a method of making an implant comprising: (a) providing a polymeric material; (b) blending the polymeric material with antibiotic(s); (c) providing a second polymeric material; (d) blending the second polymeric material with a cross-linking agent; (e) layering the antibiotic-blended polymeric material and the cross-linking agent-blended second polymeric material; and (f) consolidating the layered polymeric materials, thereby obtaining a cross-linked implant with antibiotic-rich regions.

In one embodiment the first and second polymeric material are the same, for example, the first and second polymeric materials are UHMWPE. In one embodiment the at least one therapeutic agent is vancomycin. In one embodiment the cross-linking agent is 2,5-Di(tert-butylperoxy)-2,5-dimethyl-3-hexyne (P130). In one embodiment the first polymeric material is blended with rifampin and vancomycin. In another embodiment the first and second polymeric materials are pre-mixed with antioxidant, such as vitamin E.

In an embodiment, the invention provides a method of making a therapeutic implant comprising: (a) providing a polymeric material; (b) blending the polymeric material with at least 6 wt % of antibiotic(s); (c) consolidating the anti-biotic-blended polymeric material, thereby obtaining a therapeutic implant; and (d) sterilizing the therapeutic implant.

In another embodiment, the invention provides a method of making a therapeutic implant comprising: (a) providing a polymeric material; (b) blending the polymeric material with at least 6 wt % of antibiotic(s); (c) providing a second material; (d) layering the antibiotic-blended polymeric material on the second material; and (e) consolidating the layered material(s), thereby obtaining a hybrid, interlocked therapeutic implant.

In one embodiment the therapeutic implant is an acetabular liner to be used in total hip arthroplasty, where the therapeutic implant is a tibial insert to be used in total knee arthroplasty. In another embodiment the therapeutic implant is a glenoid to be used in total shoulder arthroplasty. In another embodiment the therapeutic implant is a small plug to be placed in the screw holes of an acetabular cup to be used in total hip arthroplasty.

In any of the embodiments, a therapeutic medical implant or a therapeutic polymeric material can be used in conjunction with other methods in the field of application. For example, in total hip replacement, a therapeutic medical implant can be in the shape of an acetabular liner to be used as an articular surface. Alternatively, a therapeutic medical implant can be in the shape of small plugs or 'manhole covers' that can be placed in the existing screw holes of the acetabular shell.

BRIEF DESCRIPTION OF THE DRAWINGS

FIG. 1. Shows rate of vancomycin release from vancomycin blended-UHMWPE (VPE), 5 gram vancomycin in 40 gram bone cement (BC5), and 1 gram vancomycin in 40 gram bone cement (BC1).

FIG. 2. Fluorescent antibody staining for vancomycin on UHMWPE without additives (control), vancomycin-blended UHMWPE in its unirradiated form (VPE unirradiated) or after irradiation at 25-40 kGy (VPE irradiated). Green color indicating vancomycin presence is shown inside the dashed white lines.

FIG. 3. UV-Vis spectra of vancomycin eluted from unirradiated (Δ) and irradiated (■) vancomycin-blended UHMWPE. The main absorbance peak is at 281 nm in both cases.

FIG. 4. Live-dead staining for bacteria adhered to the surface of UHMWPE without additives (control) and vancomycin-blended UHMWPE in its unirradiated form (VPE unirradiated) or after irradiation at 25 and 100 kGy (VPE irradiated). Green color indicates live bacteria, red color indicates dead bacteria; the colors are shown in regions demarcated by dashed lines and single spots are shown by arrows.

FIG. 5. Shows the rate of drug elution into PBS at 37° C. from 3.3 wt % rifampin and 6.7 wt % vancomycin-blended UHMWPE (1 mm layer on 4 mm UHMWPE without additives).

FIG. 6. Shows the layered construct model simulating a peri-prosthetic infection at the implant-bone interface.

FIG. 7. Two-photon fluorescence of live and dead bacteria on the beaded titanium surfaces used in conjunction with UHMWPE without additives (control) and rifampin and vancomycin-blended UHMWPE (RVPE). Green color indicates live bacterial, red color indicates dead bacteria; the colors are shown in regions demarcated by dashed lines and single spots are shown by arrows.

FIG. 8. Percent red fluorescence (indicator of percentage of dead bacteria) vs time exposed to treatment as monitored by two photon fluorescence microscopy. RV-PE: Rifampin and vancomycin-blended UHMWPE. Negative control was prepared by exposing the bacteria cultured for 48 hours to 70% ethanol.

FIG. 9. Bioluminescence observed in mice infected with bioluminescent *S. aureus* (Xen 29) in dorsal subcutaneous pockets while being treated with UHMWPE containing no additives (control) and vancomycin (VPE). Regions where bacteria was measurable by bioluminescence were demarcated by a dashed white line and the intensity was indicated by the coloring.

FIG. 10. Bioluminescence of the dissected rabbit knee post mortem (day 21) after being treated with UHMWPE without additives (control) and vancomycin-blended UHMWPE (VPE). Color bar indicates the total amount of photon entering the camera, which positively correlates with number of bacteria. Regions where bacteria was measurable by bioluminescence were demarcated by a dashed white line and the intensity was indicated by the coloring.

FIG. 11. Bioluminescence of the mice after being injected with bacterial and treated with UHMWPE without additives (control) and rifampin and vancomycin-blended UHMWPE (RVPE). Color bar indicates the total amount of photon entering the camera, which positively correlates with number of bacteria. Regions where bacteria was measurable by bioluminescence were demarcated by a dashed white line and the intensity was indicated by the coloring.

FIG. 12. Bioluminescence of the dissected rabbit knee post mortem (day 21) after being treated with UHMWPE without additives (control) and rifampin and vancomycin-blended UHMWPE (RVPE). Color bar indicates the total amount of photon entering the camera, which positively correlates with number of bacteria. Regions where bacteria was measurable by bioluminescence were demarcated by a dashed white line and the intensity was indicated by the coloring.

FIG. 13. Shows two photon fluorescence of live and dead bacteria on beaded titanium surfaces of the titanium rods retrieved from rabbits where treatment was in conjunction with a UHMWPE without additives (control) or a rifampin and vancomycin-blended UHMWPE. Green color indicates live bacteria, red color indicates dead bacteria. Regions where bacteria was measurable by fluorescence were demarcated by a dashed white line and the coloring was indicated.

FIG. 14. Shows consolidated, layered, therapeutic UHMWPE implant (tibial insert). Therapeutic agent-blended layer is on the bottom.

FIG. 15. Shows consolidated, layered, therapeutic UHMWPE implant (acetabular cup: side view (A) and top view (B)).

FIG. 16. Schematic examples of a therapeutic medical implant used in the form of a 'manhole cover' in conjunction with an acetabular shell in total hip replacement (a) and with an internal fixation plate in bony fracture fixation (b).

Color photographs of FIGS. 2, 4, 7, and 9 to 13 are filed with U.S. Provisional Patent Application No. 62/254,409, filed Nov. 12, 2015, which identify the colors indicated in the brief description of the drawings and in this disclosure. All original color drawings filed with U.S. Provisional Patent Application No. 62/254,409 are hereby incorporated by reference.

DETAILED DESCRIPTION OF THE INVENTION

"Polymeric material" refers to large molecules or macro-molecules composed of many repeating subunits. "Polymeric material" includes polyolefins such as polyethylene or polypropylene. Polyethylene can include low density polyethylene(s), and/or linear low density polyethylene(s) and/or high density polyethylene(s) and/or ultrahigh molecular weight polyethylene(s) or mixtures thereof. For example, ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. Nos. 5,879,400 and 6,641,617, EP0881919, WO2001/005337, and WO1999/029793. The term "polyethylene article" or "polymeric article" or "polymer" generally refers to articles comprising any "polymeric material" disclosed herein.

The term "polymeric materials" or "polymer" also include hydrogels, such as poly (vinyl alcohol), poly (acrylamide), poly (acrylic acid), poly(ethylene glycol), blends thereof, or interpenetrating networks thereof, which can absorb water such that water constitutes at least 1 to 10,000% of their original weight, typically 100 wt % of their original weight or more or 99% or less of their weight after equilibration in water.

"Polymeric material" or "polymer" can be in the form of resin, flakes, powder, consolidated stock, implant, and can contain additives such as antioxidant(s) or therapeutic agents. The "polymeric material" or "polymer" also can be a blend of one or more of different resin, flakes or powder containing different concentrations of additive(s) such as antioxidants and/or therapeutic agents and/or a chemical crosslinking agents and/or anticrosslinking agents and/or crosslinking enhancers. The blending of resin, flakes or powder can be achieved by the blending techniques known in the art. The "polymeric material" also can be a consolidated stock of these blends.

"Anticrosslinking agent" is used to describe additives which can hinder cross-linking when added to be polymeric material. Some free radical scavengers can act as anticrosslinking agents. Some other chemicals such as solvents can also act as anticrosslinking agents. "Crosslinking enhancer" is used to describe additives which can enhance or increase crosslinking when added to the polymeric material. Some chemicals with unsaturated groups such as acetylene or some solvents can act as crosslinking enhancers.

"Polymeric materials" or "polymers" can also include structural subunits different from each other. Such polymers can be di- or tri- or multiple unit-copolymers, alternating copolymers, star copolymers, brush polymers, grafted copolymers or interpenetrating polymers. They can be essentially solvent-free during processing and use such as thermoplastics or can include a large amount of solvent such as hydrogels. Polymeric materials also include synthetic polymers, natural polymers, blends and mixtures thereof. Polymeric materials also include degradable and non-degradable polymers.

The products and processes of this invention also apply to various types of polymeric materials, for example, any polypropylene, any polyimide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), poly(ethylene glycol), poly (ethylene oxide), poly(acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

By "medical device", what is meant is an instrument, apparatus, implement, machine, implant or other similar and related article intended for use in the diagnosis, treatment, mitigation, cure, or prevention of disease in humans or other animals. An "implantable device" is a medical device intended to be implanted in contact with the human or other animal for a period of time. "Implant" refers to an "implantable medical device" where a medical device, is placed into contact with human or animal skin or internal tissues for a prolonged period of time, for example at least 2 days or more, or at least 3 months or more or permanently. Implants can be made out of metals, ceramic, polymers or combinations thereof. They can also comprise fluids or living tissues in part or in whole. An "implant" can refer to several components together serving a combined function such as "total joint implant" or it can refer to a single solid form such as an "acetabular cup" as a part. The term 'medical implant' refers to a medical device made for the purpose of implantation in a living body, for example and animal or human body. The medical implants include but are not limited to acetabular liners, tibial inserts, glenoid components, patellar components, and other load-bearing, articular components used in total joint surgery. While medical implants can be load-bearing to some extent some bear more load than others. For instance, a tibial insert bears more load than a man-hole cover implant used to cover screw holes in acetabular shells. The term "permanent device" refers to what is known in the art that is intended for implantation in the body for a period longer than several months. Permanent devices include medical implants or devices, for example, acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts. The term "medical implant" refers to what is known in the art as a device intended for implantation in animals or humans for short or long term use. The medical implants, according to an aspect of the invention, comprises medical devices including acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts, fracture plates.

The term "cross-linking" refers to what is known in the art as processes that result in the covalent bonding of the parts of a material, for example polymer chains in a polymeric material. In the case of UHMWPE, which is a semi-crystalline polymer, there is covalent bonding of the polymer chains of the polymeric material. For instance, the cross-link density of polyolefins, such as polyethylene can be measured by swelling a roughly 3×3×3 mm cube of polymeric material in xylene. The samples are weighed before swelling in xylene at 130° C. for 2 hours and they are weighed immediately after swelling in xylene. The amount of xylene uptake is determined gravimetrically, and then converted to volumetric uptake by dividing by the density of xylene; 0.75 g/cc. By assuming the density of polyethylene to be approximately 0.94 g/cc, the volumetric swell ratio of cross-linked UHMWPE is then determined. The cross-link density is calculated by using the swell ratio as described in Oral et al., *Biomaterials* 31: 7051-7060 (2010) and is reported in mol/ $m^3$. The term 'cross-linked' refers to the state of polymeric material that is cross-linked to any level.

Peroxides are a group of chemicals with the peroxide functional group. General peroxide categories include inorganic peroxides, organic peroxides, diacyl peroxides, peroxyesters, peoxydicarbonates, dialkyl peroxides, ketone peroxides, peroxyketals, cyclic peroxides, peroxymonocarbonates and hydroperoxides. They contain an easily breakable O—O bond that can dissociate/decompose into free radicals when heated and cause cross-linking in polyolefins; therefore peroxides are referred to as part of a family of "cross-linking agents" in this context. Peroxides in this invention can be selected from any peroxide, for example, benzoyl peroxide, dicumyl peroxide, methyl ethyl ketone peroxide, acetone peroxide, 2,5-Di(tert-butylperoxy)-2,5-dimethyl-3-hexyne (Luperox®130, P130), 3,3,5,7,7-pentamethyl-1,2,4 trioxepane (Trigonox® 311), etc. or mixtures thereof. Other examples of peroxides are dilauryl peroxide, methyl ether ketone peroxide, t-amyl peroxyacetate, t-butyl hydroperoxide, t-amyl peroxybenzoate, D-t-amyl peroxide, 2,5-Dimethyl 2,5-Di(t-butylperoxy)hexane, t-butylperoxy isopropyl carbonate, succinic acid peroxide, cumene hydroperoxide, 2,4-pentanedione peroxide, t-butyl perbenzoate, diethyl ether peroxide, acetone peroxide, arachidonic acid 5-hydroperoxide, carbamide peroxide, tert-butyl hydroperoxide, t-butyl peroctoate, t-butyl cumyl peroxide, Di-sec-butyl-peroxydicarbonate, D-2-ethylhexylperoxydicarbonate, 1,1-Di(t-butylperoxy)cyclohexane. Other examples of peroxides are members of the Luperox® family supplied by Arkema. Other examples of peroxides are 1,1-Di(tert-butylperoxy)-3,3,5-trimethylcyclohexane, 2,5-Dimethyl-2,5-di(tert-butylperoxy)hexane, 3,3,5,7,7-Pentamethyl-1,2,4-trioxepane, Butyl 4,4-di(tert-butylperoxy) valerate, Di(2,4-dichlorobenzoyl) peroxide, Di(4-methylbenzoyl) peroxide, Di(tert-butylperoxyisopropyl) benzene, tert-Butyl cumyl peroxide, tert-Butyl peroxy-3,5,5-trimethylhexanoate, tert-Butyl peroxybenzoate, tert-Butylperoxy 2-ethylhexyl carbonate. Other examples of peroxides are members of the Trigonox™ or Perkadox™ family supplied by Akzo Nobel.

A "crosslinking agent" is a compound which can cause cross-linking in polymeric materials. Most often, cross-linking of the polymer follows a trigger which initiates the cross-linking process. For example, crosslinking can be initiated by irradiation with or without the presence of a crosslinking agent. Crosslinking also can be initiated by 'chemical' means using a crosslinking agent. In the case of peroxides as cross-linking agent(s), heating to a temperature where the peroxide decomposes into free radicals, which are then transferred onto the polymer and initiate recombination reactions causing cross-linking, is required. Methods of 'chemical crosslinking' or cross-linking using crosslinking agent(s) is described in US Publication No. 20160250779, US Publication No. 20160215117, and WO2013/151960A2, which are hereby incorporated by reference in their entireties. In other cases, other stimuli may be used to trigger the reaction such as the application of ultraviolet light, heat, pressure or vacuum, contact with a particular solvent, or irradiation or combinations thereof. In this invention, the cross-linking agents used are often those that are commercially available and may contain impurities. In some embodiments, the cross-linking agents may be 100% pure or less. In some embodiments, the cross-linking agents are 80%, 85%, 90%, 91%, 92%, 93%, 94%, 95%, 96%, 97%, 98%, or 99% pure.

The definition of crosslinking agent herein differs somewhat from what is known in the art. Typically, a crosslinking agent is defined as a compound which can chemically attach to two or more points on the polymeric material, creating a linkage between the same or different polymer chains. We are using a more general definition where the crosslinking agent is also a compound that can initiate the processes that lead to the crosslinking of the polymeric material and the compound may or may not itself chemically attach to the polymer. For instance, the cross-linking agent may have a free radical, which may abstract a hydrogen from the polymeric material, creating a free radical on the polymeric material; subsequently such free radicals on the polymeric material can react with each other to form a cross-linked without chemically attaching the cross-linking agent to the polymeric material. In some embodiments, the unreacted cross-linking agent and/or the byproducts of the cross-linking agent are partially or fully extracted from the polymeric material after cross-linking. This extraction, among other methods, can include solvent extraction, emulsified solvent extraction, heat, and/or vacuum.

The term "additive" refers to any material that can be added to a base polymeric material in less than 50 wt/wt %. This material can be an organic or inorganic material with a molecular weight less than that of the base polymer. An additive can impart different properties to the polymeric material, for example, it can be a therapeutic agent, a nucleating agent, a cross-linking agent, an anticrosslinking agent or an antioxidant or combinations thereof. Concentrations can be from 0.001 wt % to 50 wt %, or any value thereabout or therebetween, or from 0.01 wt % to 20 wt %, or from 0.1 wt % to 10 wt %, or 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 wt %, or more.

The term "nucleating agent" refers to an additive known in the art, an organic or inorganic material with a molecular weight less than that of the base polymer, which increases the rate of crystallization in the polymeric material. Typically, organocarboxylic acid salts, for example calcium carbonate, are good nucleation agents for polyolefins. Also, nucleating agents are typically used in small concentrations such as 0.5 wt %.

The term "peak melting temperature" or "peak melting point" refers to what is known in the art as the melting transition of a polymeric material, where the material goes to a transition from a solid to a melt state. In a semi-crystalline material such as UHMWPE, this transition can overlap with the melting temperature of its crystalline portion. It can be determined using a differential scanning calorimeter at a heating rate of 10° C./min from −20° C. to 200° C. The peak melting temperature for UHMWPE is generally about 135° C. to about 140° C., or can be about 144° C. to about 147° C. if it contains extended chain crystals.

The term "therapeutic agent" refers to what is known in the art, that is, a chemical substance or a mixture thereof capable of eliciting a healing reaction from the human body. A therapeutic agent can be referred to also as a "drug" in this context. The therapeutic agent can elicit a response that is beneficial for the human or animal. Examples of therapeutic agents are antibiotics, anti-inflammatory agents, anesthetic agents, anticoagulants, hormone analogs, contraceptives, vasodilators, vasoconstrictors, or other molecules classified as drugs in the art. A therapeutic agent can sometimes have multiple functions.

Examples of therapeutic agents are antimicrobials such as Gatifloxacin, gemifloxacin, moxifloxacin, levofloxacin, pefloxacin, ofloxacin, ciprofloxacin, aztreonam, meropenem, imipenem, ertapenem, doripenem, piperacillin, Piperacillin-Tazobactam, Ticarcilin-Clavulanic acid, Ticarcillin, ampicillin-sulbactam, amoxicillin-clavulanic acid, ampicillin-amoxicillin, cloxacillin, nafcillin, oxacillin, methicillin, penicillin V, penicillin G, cefpodox, cefdinir, cefditoren, ceftibuten, cefixime, cefuroxime axetil, cefprozil, cefaclor, loracarbef, cephalexin, cefadroxil, cefepime, ceftazidime, ceftaroline, ceftriaxone, ceftizoxime, cefotaxime, cefuroxime, cefuroxime acetil, cefaclor-CD, cefoxitin, cefotetan, cefazolin, cefdinir, cefditoren pivoxil, cefixime, cefpodoxime proxetil, ceftobiprole, colistimethate, linezolid, quinupristin-dalfopristin, metronidazole, rifampin, fosfomycin, nitrofurantoin, TMP-SMX, trimethoprim, fusidic acid, telavancin, teicoplanin, Vancomycin HCl, vancomycin free base, daptomycin, tigecycline, minocycline, doxycycline, telithromycin, clarithromycin, azithromycin, azithromycin ER, erythromycin, clindamycin, chloramphenicol, amikacin, tobramycin, gentamycin, aztreonam, kanamycin, tetracycline, tetracycline HCl, polymyxin B, rifaximin, tigecycline, amphotericin B, fluconazole, itraconazole, ketoconazole, posaconazole, voriconazole, anidulafungin, caspofungin, flucytosine, micafungin, capreomycin, cycloserine, ethambutol, ethionamide, isoniazid, para-aminosalocylic acid, pyrazinamide, rifabutin, rifapentine, streptomycin, albendazole, artemether/lumefantrine, atovaquone, dpasone, ivermectin, mefloquine, miltefosine, nitazoxanide, proguanil, pytimethamine, praziquantel, tinidazole. Antiviral such as acyclovir, cidofovir, probenecid, entecavir, famciclovir, foscarnet, ganciclovir, oseltamivir, peramivir, ribavirin, rimantadine, telbiudine, valacyclovir, valgancciclovir, abacavir, atazanavir, darunavir, delavirdine, didanosine, efavirenz, emtricitabine, enfuvirtide, etravirine, fosamprenavir, indinavir, lamivudine, lopinavir, maraviroc, nelfinavir, nevirapine, raltegravir, ritonavir, sasquinavir, stavudine, tenofovir, tipranavir, zidovudine. Antifibrinolytics such as C-aminocaproic acid, tranexamic acid, lysine, aprotinin. Antineoplastics such as mechlrethamine, phenylalanine mustard, chlorambucil, cyclophosphamide, busulfan, triethylene-thiophosphoramide, carmustine, DTIC, methotrexate, 5-fluorouracil, 6-mercaptopurine, vincristine, procarbazone, prednisone, acivicin, aclarubicin, acodazole, acronine, adozelesin, alanosine, alpha-Tgdr, altretamine, ambomycin, amentantrone acetate, aminopterin, aminothiadiazole, amsacrine, anguinide, aniline mustard, anthramycin, azaribine, 5-aza-2'Deoxycytidine, 8-azaguanine.

The term "irradiation" refers to what is known in the art as exposing a material to radiation, for example ionizing radiation such as a gamma, electron, X-ray or ultraviolet (UV) radiation. 'Radiation cross-linking' refers to a radiation process intended to cross-link a material as a result of irradiation, for example exposing UHMWPE to gamma irradiation to cross-link the material. It also refers to the cross-linking in the material that has resulted from a radiation process. The radiation dose used can be from 0.0001 kGy to 100,000 kGy, or any value thereabout or therebetween, or 0.1 kGy to 1000 kGy, or from 1 kGy to 1000 kGy, or from 10 kGy to 1000 kGy, or from 25 kGy to 1000 kGy, or from 50 kGy to 1000 kGy, or from 100 kGy to 1000 kGy, or from 1 kGy to 300 kGy, or about 65 kGy, or about 75 kGy, or about 85 kGy, or about 100 kGy, or about 150 kGy, or about 175 kGy, or about 200 kGy. The radiation dose rate can be from 0.001 kGy/min to 100,000 kGy/min, or any value thereabout or therebetween, or from 0.1 kGy/min to 100 kGy/min, or from 1 kGy/min to 50 kGy/min, or about 25 kGy/min, or about 10 kGy/min, or about 100 kGy/min. Irradiation can be done in air, in vacuum, or partial gas environments, for example mixtures of oxygen and nitrogen. It can also be done in inert gas or partial inert gas. It can also be done at ambient temperature, or below or above ambient temperature. It can be done at elevated temperatures above ambient temperature. Irradiation temperature can be from −100° C. to 1000° C., or any value thereabout or therebetween, or from 0° C. to 500° C. or from 20° C. to 200° C. or from 25° C. to 150° C., or at about 25° C., or about 70° C., or about 100° C., or about 120° C., or about 125° C.

Methods of "exposing to radiation" or "irradiation" are described, for example in U.S. Pat. No. 7,381,752 (Muratoglu), U.S. Pat. No. 7,858,671 (Muratoglu et al.) and U.S. Pat. No. 6,641,617 (Merrill et al.). Also, methods of irradiation and treatments after irradiation are described, for example in U.S. Pat. No. 7,431,874 (Muratoglu et al.), U.S. Pat. No. 6,852,772 (Muratoglu et al.), U.S. Pat. No. 8,420,000 (Muratoglu et al.), U.S. Pat. No. 8,461,225 (Muratoglu et al.) and U.S. Pat. No. 8,530,057 (Muratoglu et al.).

The penetration depth of radiation can be controlled by methods such as those described in U.S. Pat. No. 7,381,752 (Muratoglu) and WO2013/170005 A1 (US Publication No. 20150151866). Electron irradiation, in general, results in more limited dose penetration depth, but requires less time and, therefore, reduces the risk of extensive oxidation if the irradiation is carried out in air. In addition if the desired dose levels are high, for instance 20 MRad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 MRad melt-irradiation can be completed in for instance less than 10 minutes. The penetration of the electron beam depends on the beam energy measured by million electron-volts (MeV). Most polymers exhibit a density of about 1 $g/cm^3$, which leads to the penetration of about 1 cm with a beam energy of 2-3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively.

The term "blending" refers to what is known in the art; that is, mixing of different components, often liquid and solid or solid and solid to obtain a homogeneous mixture of the components. Blending generally refers to mixing of a polymeric material in its pre-consolidated form with an additive. If both constituents are solid, blending can be done by using other component(s) such as a liquid to mediate the mixing of the two components, after which the liquid is removed by evaporating. If the additive is liquid, for example α-tocopherol, then the polymeric material can be mixed with large quantities of the liquid. This high concentration blend can be diluted down to desired concentrations with the addition of lower concentration blends or virgin polymeric material without the additive to obtain the desired concentration blend. This technique also results in improved uniformity of the distribution of the additive in the polymeric material. Methods of blending additives into polymeric material are described, for example in U.S. Pat. Nos. 7,431,874, 9,168,683, 8,425,815, 9,273,189, and WO2007/024684A2 (Muratoglu et al.).

The term "Diffusion" refers to what is known in the art; that is, the net movement of molecules from an area of high concentration to an area of low concentration. In these embodiments, it is defined to be interchangeably used with 'doping by diffusion'. The term "doping" refers to a general process well known in the art (see, for example, U.S. Pat. Nos. 6,448,315 and 5,827,904), that is introducing additive(s) to a material. Doping may also be done by diffusing an additive into the polymeric material by immersing the polymeric material by contacting the polymeric material with the additive in the solid state, or with a bath of the additive in the liquid state, or with a mixture of the additive in one or more solvents in solution, emulsion, suspension, slurry, aerosol form, or in a gas or in a supercritical fluid. The doping process by diffusion can involve contacting a polymeric material, medical implant or device with an additive, such as vancomycin, for about an hour up to several days, preferably for about one hour to 24 hours, more preferably for one hour to 16 hours. The doping time can be from a second to several weeks, or it can be 1 minute to 24 hours, or it can be 15 minutes to 24 hours in 15 minute intervals. The environment for the diffusion of the additive (bath, solution, emulsion, paste, slurry and the like) can be heated to room temperature or up to about 200° C. and the doping can be carried out at room temperature or up to about 200° C. For example, when doping a polymeric material by an antioxidant, the medium carrying the antioxidant can be heated to 100° C. and the doping is carried out at 100° C. Similarly, when doping a polymeric material with therapeutic agent(s), the medium carrying the therapeutic agent(s) can be cooled or heated. Or the doping can be carried out at 5, 10, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 230, 240, 250, 260, 270, 280, 290, 300, 320 and 340° C., and any value thereabout or therebetween. If the additive is a peroxide, the doping temperature may be below the peroxide initiation temperature, at the peroxide initiation temperature or above the peroxide initiation temperature or parts of the doping process may be done at different temperatures. A polymeric material incorporated with an additive by diffusion in such a way is termed an "additive-diffused" polymeric material. If the additive is a therapeutic agent, a polymeric material incorporated with the additive is termed a "therapeutic agent-diffused" polymeric material. Diffusion of additives such as antioxidants by high temperature doping and homogenization methods are described in Muratoglu et al. (U.S. Pat. Nos. 7,431,874 and 9,370,878), which are incorporated by reference in its entirety.

The term "antioxidant" refers to what is known in the art as (see, for example, U.S. Pat. No. 8,933,145, WO2001/80778, and U.S. Pat. No. 6,448,315). Alpha- and delta-tocopherol; propyl, octyl, or dodecyl gallates; lactic, citric, ascorbic, tartaric acids, and organic acids, and their salts; orthophosphates, lycopene, tocopherol acetate are generally known form of antioxidants. Antioxidants are also referred as free radical scavengers, include: glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids, including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1330; Irgafos® family including Irgafos® 168; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. Antioxidants/free radical scavengers can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination.

The term "consolidation" refers generally to processes used to convert the polymeric material resin, particles, flakes, i.e. small pieces of polymeric material into a mechanically integral large-scale solid form, which can be further processed, by for example machining in obtaining articles of use such as medical implants. Methods such as injection molding, extrusion, compression molding, isostatic pressing (hot or cold), or other methods known in the art can be used. In the present invention, consolidation of layers of polymeric material having different additives is described.

Consolidation can be performed by "compression molding". In some instances consolidation can be interchangeably used with compression molding. The molding process generally involves:

i. heating the polymeric material to be molded,
ii. pressurizing the polymeric material while heated,
iii. keeping at temperature and pressure, and
iv. cooling down and releasing pressure.

Heating of the polymeric material can be done at any rate. Temperature can be increased linearly with time or in a step-wise fashion or at any other rate. Alternatively, the polymeric material can be placed in a pre-heated environment. In some embodiments, the polymeric material is placed into a mold for consolidation and he process (steps i-iv) is started without pre-heating. The mold for the consolidation can be heated together or separately from the polymeric material to be molded. Steps (i) and (ii), i.e. heating and pressurizing before consolidation can be done in multiple steps and in any order. For example, polymeric material can be pressurized at room temperature to a set pressure level 1, after which it can be heated and pressurized to another pressure level 2, which still may be different from the pressure or pressure(s) in step (iii). Step (iii), where a high temperature and pressure are maintained is the 'dwell period' where a major part of the consolidation takes place. One temperature and pressure or several temperatures and pressures can be used during this time without releasing pressure at any point. For example, dwell temperatures in the range of 135 to 350° C. and dwell pressures in the range of 0.1 MPa to 100 MPa or up to 1000 MPa, or any value thereabout or therebetween, can be used. The dwell time can be from 1 minute to 24 hours, more preferably from 2 minutes to 1 hour, most preferably about 10 minutes. The temperature(s) at step (iii) are termed 'dwell' or 'molding' temperature(s). The pressure(s) used in step (iii) are termed 'dwell' or 'molding' pressure(s). The order of cooling and pressure release (step iv) can be used interchangeably. In some embodiments the cooling and pressure release may follow varying rates independent of each other. In some embodiments, consolidation of polymeric resin or blends of the resin with additive(s) are achieved by compression molding. The dwell temperature and dwell time for consolidation can be changed to control the amount of integration.

Compression molding can also follow "layering" of different polymeric material; in these instances it is termed "layered molding". This refers to consolidating a polymeric material by compression molding one or more of its pre-molded and resin forms, which may be in the form of flakes, powder, pellets or the like or consolidated or pre-molded forms in layers. This may be done such that there can be distinct regions in the consolidated form containing different concentrations of additives such as antioxidant(s), therapeutic agent(s) and/or crosslinking agent(s). Layering can be done any method that deposits desired polymeric material in desired locations. These methods may include pouring, scooping, painting, brushing spraying. This deposition can be aided by materials, templates and such supporting equipment that do not become an eventual part of the consolidated polymeric material. Whenever a layered-molded polymeric material is described and is used in any of the embodiments, it can be fabricated by:

(a) layered molding of polymeric resin powder or blends of polymeric material containing a specific additive(s) where one or more layers contain the additive and one or more layers do not contain the additive(s);

(b) molding together of layers of polymeric material containing different or identical concentration of additives such as therapeutic agent(s), antioxidant(s) and/or crosslinking agent(s).

Layering and spatial control of additive concentrations and polymeric material morphology are described in WO2008/092047A1, U.S. Pat. Nos. 9,433,705, and 8,569,395 (Muratoglu et al.), which are incorporated by reference in their entireties.

One or more of the layers can be treated before or during molding by heating, or high temperature melting. Methods of high temperature melting are described in WO2010/096771A2, U.S. Pat. No. 8,933,145 (Oral et al.), which are incorporated by reference in their entireties.

The layer or layers to be molded can be heated in liquid(s), in water, in air, in inert gas, in supercritical fluid(s) or in any environment containing a mixture of gases, liquids or supercritical fluids before pressurization. The layer or layers can be pressurized individually at room temperature or at an elevated temperature below the melting point or above the melting point before being molded together. The temperature at which the layer or layers are pre-heated can be the same or different from the molding or dwell temperature(s). The temperature can be gradually increased from pre-heat to mold temperature with or without pressure. The pressure to which the layers are exposed before molding can be gradually increased or increased and maintained at the same level.

During consolidation, different regions of the mold can be heated to different temperatures. The temperature and pressure can be maintained during molding for 1 second up to 1000 hours or longer. During cool-down under pressure, the pressure can be maintained at the molding pressure or increased or decreased. The cooling rate can be, for example, 0.0001° C./minute to 120° C./minute or higher, or any value thereabout or therebetween. Cooling can be done at any rate. The cooling rate can be different for different regions of the mold. After cooling down to about room temperature, the mold can be kept under pressure for 1 second to 1000 hours, or any value thereabout or therebetween. Or the pressure can be released partially or completely at an elevated temperature.

In some embodiments, the consolidated polymeric material is fabricated through "direct compression molding" (DCM), which is compression molding using parallel plates or any plate/mold geometry which can directly result in an implant or implant preform. Preforms are generally over-sized versions of implants, where some machining of the preform can give the final implant shape. In some embodiments certain features of the final implant shape may be machined after direct compression molding.

In some embodiments, the pre-molded polymeric material is subjected to high temperature melting and subsequently direct compression molded. The direct compression molded polymeric material may be in its final implant shape. In some embodiments certain features of the final implant shape may be machined after direct compression molding. In certain embodiments, the pre-molded polymeric material contains cross-linking agents. In some embodiments the pre-molded polymeric material is subjected to irradiation before the subsequent direct compression molding.

Compression molding can also be done such that the polymeric material is directly compression molded onto a second surface, for example a metal or a porous metal to result in an implant or implant preform. This type of molding results in a "hybrid interlocked polymeric material" or "hybrid interlocked medical implant preform" or "hybrid interlocked medical implant". Molding can be conducted with a second piece, for example a metal that becomes an integral part of the consolidated polymeric article. For example, a combination of antioxidant-containing polyethylene resin, powder, or flake and virgin polyethylene resin, powder or flake is direct compression molded into a metallic acetabular cup or a tibial base plate. The porous tibial metal base plate is placed in the mold, antioxidant blended polymeric resin, powder, or flake is added on top. Prior to consolidation, the pores of the metal piece can be filled with a waxy or plaster substance through half the thickness to achieve polyethylene interlocking through the other unfilled half of the metallic piece. The pore filler is maintained through the irradiation and subsequent processing (for example peroxide diffusion) to prevent infusion of components in to the pores of the metal. In some embodiments, the article is machined after processing to shape an implant. In some embodiments, there is more than one metal piece integral to the polymeric article. The metal(s) may be porous only in part or non-porous. In another embodiment, one or some or all of the metal pieces integral to the polymeric article is a porous metal piece that allows bone in-growth when implanted into the human body. In an embodiment, the porous metal of the implant is sealed using a sealant to prevent or reduce the infusion of antioxidant/peroxide (in diffusion steps after consolidation) into the pores during the selective doping of the implant. Preferably, the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch. In these embodiments, the polymeric material, which is molded directly onto a second surface to form the hybrid interlocked polymeric material, maybe a pre-molded polymeric material with or without additives and/or cross-linking agents. In such embodiments the pre-molded polymeric material may be subjected to high temperature melting and/or radiation cross-linking.

The term "heating" refers to bringing a material to a temperature, generally a temperature above that of its current state. It can also refer to maintaining the temperature for a period of time, that is, in some instances it can be used interchangeably with 'annealing'. Heating can be done at any rate. The heating rate can be, for example, from 0.001° C./min to 1000° C./min, or any value thereabout or therebetween, or it can be between 0.1° C./min to 100° C./min, or it can be from 0.5° C./min to 10° C./min, or it can be any rate from 1° C./min to 50° C./min in 1° C. intervals. The heating can be done for any duration. Heating time can be from 0.1 minutes to 100 years or from 1 minute to 24 hours or from 1 minute to 12 hours, or 30 minutes to 10 hours, or 5 hours, or 6 hours, or 8 hours, or any value thereabout or therebetween.

The term "cooling" refers to bringing a material to a temperature, generally a temperature below that of its current state. It can also refer to maintaining the temperature for a period of time, that is, in some instances it can be used interchangeably with 'annealing'. Cooling can be done at any rate. The cooling rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals, or 2.5° C./min, or any value thereabout or therebetween. The cooling can be done for any duration. Cooling time can be from 0.1 minutes to 100 years or from 1 minute to 24 hours or from 1 minute to 12 hours, or 30 minutes to 10 hours, or 1 hour, or 2 hours, or 5 hours, or 6 hours, or 8 hours, or any value thereabout or therebetween.

The terms "about" or "approximately" in the context of numerical values and ranges refers to values or ranges that approximate or are close to the recited values or ranges such that the invention can perform as intended, such as utilizing a method parameter (e.g., time, dose, dose rate/level, and temperature), having a desired amount of antibiotics, desired degree of cross-linking and/or a desired lack of or quenching of free radicals, as is apparent to the skilled person from the teachings contained herein. This is due, at least in part, to the varying properties of polymer compositions. Thus, these terms encompass values beyond those resulting from systematic and random error. These terms make explicit what is implicit, as known to the person skilled in the art.

The term "sterile" refers to a condition of an object, for example, an interface or a hybrid material or a medical implant containing interface(s), wherein the interface is sufficiently sterile to be medically acceptable, i.e., will not cause an infection or require revision surgery. The object, for example a medical implant, can be sterilized using ionizing radiation or gas sterilization techniques. Gamma sterilization is well known in the art. Electron beam sterilization is also used. Ethylene oxide gas sterilization and gas plasma sterilization are also used. Autoclaving is another method of sterilizing medical implants. Exposure to solvents or supercritical fluids for sufficient to kill infection-causing microorganisms and/or their spores can be a method of sterilizing.

The term 'wear' refers to the removal of material from the polymeric material during articulation or rubbing against another material. For UHMWPE, wear is generally assessed gravimetrically after an initial creep deformation allowance in number of cycles of motion. The term 'wear resistant' refers to the state of a polymeric material where it has low wear. For example, the wear rate is tested on cylindrical pins (diameter 9 mm, length 13 mm) on a bidirectional pin-on-disc wear tester in undiluted bovine calf serum at 2 Hz in a rectangular pattern (5 mm×10 mm) under variable load with a maximum of 440 lbs. as described in Bragdon et al. (*J Arthroplasty* 16: 658-665 (2001)). Initially, the pins are subjected to 0.5 million cycles (MC), after which they are tested to 1.25 million cycles with gravimetric measurements approximately every 0.125 MC. The wear rate is determined by the linear regression of the weight loss as a function of number of cycles from 0.5 to 1.25 MC.

The term "surface" refers to any part of the outside of a solid-form material, which can be exposed to the surrounding liquid, gaseous, vacuum or supercritical medium. The surface can have a depth into the bulk of the material (normal to the surface planes), from several microns (μm) to several millimeters. For example, when a 'surface layer' is defined, the layer can have a thickness of several nanometers to several microns (μm) to several millimeters. For example, the surface layer can be 100 microns (100 μm) or 500 microns (500 μm) or 1000 microns (1 mm) or 2 mm or it can be between 2 and 5 mm, or any value thereabout or therebetween. The surface or surfaces can also be defined along the surface planes. For example, a 5 mm wide and 15 mm long oval section of the articulating surface of a tibial knee insert can be defined as a 'surface' to be layered with a UHMWPE containing additives. These surfaces can be defined in any shape or size and the definition can be changed at different processing step. (FIGS. 12 and 13).

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but are not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

In total joint replacements, where a peri-prosthetic joint infection (PJI) is suspected and/or confirmed (usually by joint aspiration and culture) after the primary surgery, an effective treatment is a two-stage procedure, where the joint is opened, the implants (all non-polymeric parts such as the shell for fixation into the acetabulum and the femoral stem/head and all the polymeric components such as the UHMWPE liner are removed. The joint is then debrided and washed thoroughly. Antibiotic eluting bone cement (polymethyl methacrylate or PMMA) is prepared in the operating room by mixing antibiotics with virgin bone cement and filling the resultant paste into the femoral canal and acetabular faces and forming a spacer to maintain the space in between the two. The wound is closed and the patient is treated with intravenous antibiotics for 4-6 weeks after which the antibiotics are discontinued for at least 2 weeks and the clearance of the infection is confirmed by another aspiration and culture. Once the joint is clear of the infection, the joint is re-operated upon and brand new implants are placed, usually accompanied by the use of antibiotic-eluting bone cement as a fixation aid between the joint implant and bony surfaces commensurate with bone cement's primary role. During this treatment, patients are immobilized for the duration in between the first and second surgeries because antibiotic-eluting spacers are not load-bearing.

In the present invention, methods of making antibiotic-eluting, load-bearing polymeric materials are described such that these materials can be used in conjunction with bone cement/antibiotic-eluting bone cement as a fixation aid.

In some embodiments, an antibiotic-eluting polymeric material made by the methods described herein can be made in the shape of a bearing surface, for example an acetabular liner, and can be used in a 'two stage revision for PJI'. In this application, the liner can be used instead of the antibiotic eluting bone cement spacer in the two-stage surgery described previously. This antibiotic-eluting liner can be load-bearing and therefore, the patients can be mobilized in a manner consistent with their daily lives while being treated for infection.

Alternatively, an antibiotic-eluting polymeric material made by the methods described herein can be made in the shape of a bearing surface, for example an acetabular liner, and can be used in a 'liner exchange'. In this approach, instead of going through a two-stage surgery, a patient with a suspected and/or confirmed peri-prosthetic joint infection can undergo a single surgery where only the polymeric bearing surface (for example, acetabular liner) is removed, the joint is debrided, washed thoroughly (lavage) and a new bearing surface is placed. In this approach, the new liner would be made out of the antibiotic-eluting polymeric materials described herein.

Alternatively, an antibiotic-eluting polymeric material made by the methods described herein can be made in the shape of a bearing surface, for example an acetabular liner and can be used in a 'single stage revision for PJI'. In this approach, instead of going through the two-stage surgery, a patient with a suspected and/or confirmed peri-prosthetic joint infection can undergo a single surgery where at least some but most often all of the non-polymeric implant components and the polymeric bearing surface (for example, acetabular liner) are removed, the joint is debrided, washed thoroughly (lavage) and new implants including a new bearing surface is placed.

Alternatively, an antibiotic-eluting polymeric material made by methods described herein can be made in the shape of small plug ('manhole cover') and can be used pressfit into an acetabular shell (FIG. 16). Commonly, some metallic components that come into contact with bony surfaces can have holes to accommodate screws for additional fixation strength and stability if desired. Many of these screw holes do not end up accommodating screws during the operation and are left 'as is'. One or more antibiotic-eluting polymeric materials made by the methods described herein can be placed into these holes instead of screws. These metallic components, for example in the case of an acetabular shell, can be used together with a bearing surface without antibiotics or with a bearing surface eluting antibiotics such as those made by methods described herein.

Alternatively, an antibiotic-eluting polymeric material made by methods described herein can be made the shape of small plugs and can be used pressfit into the bearing surface. For example, a tibial insert, which is the polymeric bearing surface used in a total knee replacement, can be made with small indentations on its backside (which would typically be in direct contact with the tibial base tray or be cemented into the tibial plateau) into which the small plugs can fit. The bearing surface can then be fit with the antibiotic-eluting plug(s) and placed into a tibial base tray (which comes into contact with the bony surfaces on the tibial side of the implant with or without bone cement as a fixation aid).

While present inventive concepts have been described with reference to particular embodiments, those of ordinary skill in the art will appreciate that various substitutions and/or other alterations may be made to the embodiments without departing from the spirit of present inventive concepts.

Accordingly, the descriptions provided herein are meant to be exemplary, and does not limit the scope of present inventive concepts.

A number of illustrative and non-limiting examples are provided herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

EXAMPLES

Various methods of making cross-linked polymeric materials containing antioxidants according to the invention are described in more detail in the following illustrative examples. Although the examples may represent only selected embodiments of the invention, it should be understood that the following examples are illustrative and not limiting.

Example 1. Blending a Polymeric Material with an Antioxidant

Vitamin E (D,L-α-tocopherol) was dissolved in isopropanol with a concentration of 20 g/L. Medical grade GUR 1050 UHMWPE powder was blended and stirred with the vitamin E/isopropanol solution to make a homogeneous blend with a concentration of 2 wt %. This blend was dried in a convection oven under vacuum at 60° C. for 7 days and diluted with GUR 1050 powders into concentrations ranging from 0-1 wt % of vitamin E (0, 0.1, 0.2, 0.3, 0.5, 0.6, 0.8 and 1 wt %). The resulting was an antioxidant-blended UHMWPE, or a vitamin E-blended UHMWPE.

Example 2. Blending a Polymeric Material with Therapeutic Agents

Vancomycin-HCl (1 gram) was crushed with mortar and pestle and then passed through a 75 μm sieve. Vancomycin-HCl powder was then mechanically mixed for 30 minutes at room temperature. GUR1020 UHMWPE GUR 1020 (12 grams) was added to the Rifampin and Vancomycin-HCl mixture and mechanically mixed/blended for 30 minutes at room temperature. The resultant was a UHMWPE with 6 wt % vancomycin.

Example 3. In Vitro Elution Profiles of Therapeutic Agent-Blended UHMWPE

Vancomycin-HCl (1.5 gram) was crushed with mortar and pestle and then passed through a 75 μm sieve. Then, it was mechanically mixed with GUR1020 UHMWPE powder (23.5 grams) for 30 minutes at room temperature to obtain a 6 wt % vancomycin-blended UHMWPE and consolidated by compression molding. Circular discs with diameter of 5 mm and thickness of 3 mm (n=6) were machined from consolidated vancomycin-blended UHMWPE (V-PE) prepared from an approximately 3 mm-thick vancomycin blended-UHMWPE (approximately 10.5 cm diameter). For comparison, two different concentrations of vancomycin-blended bone cement were made: 1 gram of vancomycin in 40 gram bone cement (BC1) and 5 gram of vancomycin in 40 gram bone cement (BC5). All samples were immersed separately in 1 ml of phosphate-buffered saline at 37° C. for a pre-determined time (6 hr, 24 hr, every 24 hr until one week, and once every week thereafter). After each time-point, the specimens were washed with phosphate-buffered saline and placed in a new 1 ml of phosphate-buffered saline. Concentrations of vancomycin were determined using Ultraviolet-Visible spectroscopy (UV-Vis). Rate of drug release was calculated by dividing the measured concentration with the duration the sample was contacted with phosphate-buffered saline. Rate of drug release of V-PE, BC1, and BC5 are shown in FIG. 1.

The results showed that the rate of vancomycin release of VPE was higher than that of BC1 at all-time points, and similar to that of BC5 at all time points.

Example 4. Effect of Radiation on Vancomycin-Blended UHMWPE

Vancomycin HCl-blended UHMWPE was prepared with a concentration of 6 wt % vancomycin as described in Example 3. Consolidation was performed at 170° C. for 10 min at 20 MPa. The platens were then cooled down with air down to approximately 162° C. and then cooled down with water starting at approximately 156° C. down to about room temperature to obtain an approximately 3 mm-thick puck (approximately 10.5 mm diameter). Consolidated vancomycin-blended samples (VPE) were then either used as is or gamma irradiated at 100 kGy. UHMWPE without additives was used as control. In vitro elution of samples in all three groups was conducted in phosphate buffered saline (PBS) as described in Example 3. After no detectable vancomycin could be measured through UV-Vis, the presence of vancomycin grafted onto the surface of the polymer was determined by labeling with an anti-vancomycin antibody.

To label the samples, first samples were immersed in blocking solution composed of 1% Bovine Serum Albumin in PBS (3 hr, 37° C.), and washed with phosphate buffered saline. Samples were then incubated with a primary antibody against vancomycin (mouse anti-vancomycin IgG, 1:500) in PBS at 4° C. for 2 hr. Samples were then washed 3 times with PBS, incubated in PBS for 30 minutes, and then incubated with solution of AlexaFluor 488-coupled donkey anti-mouse IgG (1:500) in PBS for 1 hr followed by 10 PBS washes and incubation in PBS for 30 minutes. Samples were then visualized using inverted fluorescence microscopy.

Representative images of the vancomycin staining of the samples from the three groups are shown in FIG. 2. The image showed overlay of the optical microscopy and the antibody-labelled vancomycin (green). Both control and V-PE unirradiated showed minimum green, indicating minimum/no vancomycin grafted to the surface of the sample. On the other hand, there was significant amount of green fluorescence on the V-PE irradiated samples, indicating presence of vancomycin grafted to the surface of the sample.

Also, the comparison of the UV absorbance of vancomycin eluted from the polymeric material with and without terminal irradiation was the same (FIG. 3); showing that vancomycin was not affected by irradiation when blended in the polymeric material.

Example 5. Effect of Vancomycin-Grafted UHMWPE on Bacterial Adhesion

Consolidated Vancomycin HCl-blended UHMWPE samples (VPE) were made as described in Example 4. Consolidated samples were then used 'as is' or were gamma irradiated at 100 kGy. UHMWPE without additives was used as control. In vitro elution of vancomycin from the samples of all three groups (Control, VPE unirradiated, VPE irradiated) were conducted as described in Example 3. After no detectable vancomycin could be measured through UV-Vis, the ability of bacteria (S. aureus) to attach to the surface of the sample was determined.

Samples (circular discs with 5 mm diameter, 3 mm thickness) were sterilized with ethylene oxide gas and placed in 15-ml Falcon tubes containing Mueller Hinton broth inoculated with $2 \times 10^5$ CFU/ml of Staphylococcus aureus (ATCC 29213). The tubes were then incubated at 37° C. for 48 hr on a rocking table at 12 cycles/min. After 48 hours, samples were then washed with gently with phosphate buffered saline (PBS) to remove the planktonic cells and then stained with Live/Dead™ BacLight™ Viability kit for 30 min to fluorescently label the bacteria. Samples are then washed with PBS to remove the nonspecific stain and the adherent bacteria were imaged with inverted fluorescence microscopy.

Representative image of bacterial adherence to the surface of the polymer is shown in FIG. 4. Both unirradiated and irradiated vancomycin HCl-blended UHMWPE ('VPE unirradiated' and 'VPE irradiated', respectively) had less bacterial adherence to the surface as compared to control. On average, 'VPE unirradiated' had 30% less bacterial adherence as compared to control, and 'VPE irradiated' had 80% less bacterial adherence as compared to control.

These results showed that irradiation after consolidation and blending did not compromise the effectiveness and therapeutic capacity of vancomycin.

Example 6. In Vitro Release Rates from UHMWPE Blended with More than One Therapeutic Agent Rifampin (0.4 gram) was crushed with mortar and pestle and then passed through 75 μm sieve. Vancomycin-HCl (0.8 gram) was crushed with mortar and pestle and then passed through a 75 μm sieve. Rifampin powder and vancomycin-HCl powders were then mechanically mixed for 30 minutes at room temperature. GUR1020 UHMWPE GUR 1020 (12 gram) was added to the Rifampin and Vancomycin-HCl mixture and mechanically mixed/blended for 30 minutes at room temperature, obtaining a 3.3 wt % rifampin and 6.7 wt % vancomycin-blended UHMWPE. 10 grams of the resulting rifampin and vancomycin-blended UHMWPE were transferred to the female part of circular stainless steel mold with diameter of 11 cm. Using a circular polycarbonate plunger, the mixture was spread evenly across the base of the mold. 25 grams of GUR 1020 UHMWPE without additives were then added to the stainless steel mold on top of the rifampin and vancomycin-blended UHMWPE. Using a new circular polycarbonate plunger, the UHMWPE GUR 1020 are spread evenly and gently to create even thickness throughout the mold without disturbing the lower layer of rifampin and vancomycin-blended UHMWPE. The male portion of the mold was then inserted into the top and the whole mold was transferred to a compression molding press with pre-heated platens.

The therapeutic agent-blended UHMWPE layered onto UHMWPE without additives was consolidated at 170° C. for 10 min at 20 MPa. The platens were then cooled down with air down to approximately 162° C. and then cooled down with water starting at approximately 156° C. down to about room temperature.

Blocks with dimension of 5 mm×5 mm×20 mm (n=6) were cut from the consolidated layered rifampin and vancomycin-blended UHMWPE (RV-PE) prepared using 10 grams of the blend and 40 grams of UHMWPE without additives resulting in a 1 mm-thick layer of blend and 4 mm-thick layer of UHMWPE without additives. Each block then consisted of a 1 mm×5 mm×20 mm RV-PE layer on top of a 4 mm×5 mm×20 mm layer of UHMWPE without additives. Each block was immersed in 1 ml of phosphate-buffered saline at 37° C. for a pre-determined time points (6 hr, 24 hr, every 24 hr until 1 week, 14 days, and 21 days) up to a total period of 9 months. After each time-point, the specimens were washed with phosphate-buffered saline and placed in a new 1 ml of phosphate-buffered saline. Concentrations of vancomycin and rifampin were determined using Ultraviolet-Visible spectroscopy (UV-Vis). Rate of drug release was calculated by dividing the measured concentration with the duration the sample was contacted with phosphate-buffered saline. Rate of drug release of both rifampin and vancomycin vs time is shown in FIG. 5.

"Vancomycin min" indicates the minimum vancomycin release rate to achieve minimum inhibitory concentration of the antibiotic (2 µg/ml) assuming an approximate clearance half-life of 3.5 hours from the joint space in the human hip. "Rifampin min" indicates the minimum rifampin release rate to achieve minimum inhibitory concentration (1 µg/ml) assuming an approximate clearance half-life of 3 hours from the joint space in the human hip. The value of vancomycin min and rifampin min are 0.3 and 0.15 µg/ml, respectively. Release rate of both vancomycin and rifampin were higher than their corresponding minimum release rates for at least 36 weeks.

Example 7. In Vitro Efficacy of Therapeutic UHMWPE in a Chronic Infection (Biofilm) Model A consolidated, layered, therapeutic polymeric material was prepared by layering 1 mm of rifampin and vancomycin-blended UHMWPE with 3 mm of UHMWPE without additives and consolidating as described in Example 6 (RV-PE). Then, the consolidated polymeric material was machined into discs (5 mm diameter). The following were also used: (1) a 4 mm-thick consolidated UHMWPE without additives, which was prepared using the same molding conditions and (2) titanium discs coated with titanium discs (10 mm diameter, 5 mm thickness, bead diameter 100 µm) and (3) cortical bone discs (10 mm diameter, 3 mm thickness).

An experiment was conducted to test whether the antibiotics blended into therapeutic UHMWPE were able to diffuse between the titanium and bone interface and effectively eliminate the bacterial biofilm. For this purpose, a construct was prepared by layering the different discs such that the RV-PE contacted the non-beaded side of the titanium discs, the beaded side of the titanium discs contacted the cortical bone. A circular stainless steel clamp with inner diameter of 10 mm was used to hold the construct together (FIG. 6).

Layered RV-PE and cortical bone disc were sterilized with ethylene oxide gas, while stainless steel clamps and titanium disc were sterilized in an autoclave. Fresh overnight liquid culture of Bioluminescent *Staphylococcus aureus* (Xen 29) was diluted to 5×10$^4$ cfu/ml. 50 µL of the liquid culture was added on top of the beaded-surface of the titanium discs to simulate an infection at an orthopaedic implant-bone interface. Cortical bone was added on top of the titanium disc seeded with bacteria and held together with the circular clamp (n=6). The constructs were then immersed in fresh Mueller-Hinton II broth and then incubated at 37° C. for 48 hr. After 48 hr of incubation, biofilm formation was measured using a bioluminescence camera. To maximize the amount of photons entering the camera, bone was aseptically detached from the titanium, washed with sterile phosphate buffered saline to remove planktonic bacteria, and then imaged. Cortical bone was placed back on top of the titanium after imaging. The six bone-titanium constructs were then divided randomly into two groups: Control UHMWPE group (n=3) and RV-PE group (n=3). Both UHMWPE without additives and RV-PE were placed under the titanium-bone construct in contact with the non-beaded surfaces of the titanium discs. Each sample was then separately placed in its own well in a 6-well plate and 5 ml of Mueller-Hinton II broth was added to each well. All samples were then incubated at 37° C. Bioluminescence was measured every 24 hr on each of the surfaces until 48 hours. Media was replaced every 24 hr. At the end of the experiment, to image the live and dead bacteria in the biofilm, all samples were then stained with a Live-Dead stain, and imaged with two-photon fluorescence microscopy.

No bioluminescence was detected for the RV-PE group on any of the surfaces. There was detectable bioluminescence in the control group on all surfaces; the bioluminescence remained similar at 24 and 48 hours for titanium and bone in the control group, but the bioluminescence on the polyethylene increased. Live-Dead imaging with two photon microscopy showed no live bacteria on any surfaces in the RV-PE group. Bacterial viability was 85-90% on both the titanium and the bone surfaces in the control groups. Representative two photon images of the control and treated groups are shown in FIG. 7.

These results showed that in this in vitro model of biofilm formation at the bone-orthopedic implant interface, rifampin and vancomycin elution from a UHMWPE implant component blended with these agents could eliminate the bacteria at the bone-implant interface, with which the therapeutic UHMWPE implant had no contact.

Thirty six bone-titanium constructs with Xen 29 biofilm were made as described above. All biofilm were grown for 48 hours prior to treatment with either UHMWPE without therapeutics or therapeutic UHMWPE. The bone-titanium constructs with Xen 29 biofilm were divided equally into two groups: Control and rifampin and vancomycin-blended UHMWPE (RV-PE). Samples from each group were then further divided into five subgroups: 6 hr, 24 hr, 48 hr, 72 hr, 96 hr, 1 week, and 2 weeks based on the contact time of the constructs with the UHMWPE surfaces. At the end of the contact period, samples were stained with live dead stain and imaged with two photon fluorescence microscopy to determine the viability of bacteria.

At 6 hours of contact, percent dead bacteria in both non-therapeutic and RV-PE groups were not statistically different (FIG. 8). However, after 24 hr, 50% of bacteria in the RV-PE group were dead, compared to 15% of bacteria in the control group. All bacteria in the RV-PE group were dead by 96 hr, while bacteria in the control group retained about 85% viability throughout the 2 week study.

Example 8. Subcutaneous Implantation of a Vancomycin-Blended UHMWPE in a Mice Acute Infection Model This study was conducted to test the efficacy of vancomycin-blended UHMWPE (VPE). A construct with 6 wt % vancomycin-blended UHMWPE was prepared as described in Example 3 against bioluminescent *S. aureus* (Xen 29) in the dorsal subcutaneous pockets of BL6/C57 fully immune-competent mice. Minimum inhibitory concentration of vancomycin against Xen 29 was 1 µg/ml (Morthin, L; Li, T, Andrew, D; Vann Praagh, D; Zhang, S; Zhang, X; Alder, J. Rapid Bactericidal Activity of Daptomycin against Methicillin-Resistant and Methicillin-Susceptible *Staphylococcus aureus* Peritonitis in Mice as Measured with Bioluminescent Bacteria. *Antimicrob. Agents Chemotherapy*, 2007, 51(5): 1787-1794). Minimum inhibitory concentration of rifampin against Xen 29 was 0.01 μg/ml.

Ten mice were randomly divided into two groups: Control and VPE groups (n=5 each). Each mouse in the control group received a disc implant made from UHMWPE without additives (diameter=6 mm, thickness=3 mm) in the dorsal subcutaneous pocket, while each mouse in the VPE group received a disc implant made from VPE (diameter=6 mm, thickness=3 mm) in the dorsal subcutaneous pocket. After closure of the surgical incision using monofilament suture, mice in both groups received a subcutaneous injection of $5 \times 10^7$ cfu of Xen 29 in 50 μL 0.9% saline. This bacterial inoculation was injected adjacent to the implants. Bioluminescence was measured using an IVIS 100 imaging system 5 minutes after bacterial injection, at 3 hr, 24 hr, and 48 hr. Note that only live bacteria luminesce, and therefore the amount of live bacteria is proportional to the total bioluminescence.

At the end of study (48 hr after bacterial injection), all mice were sacrificed and implants were retrieved aseptically and placed into a sterile 15 cc Falcon tube containing 2 ml 0.9% saline. Falcon tubes containing the retrievals and saline were sonicated to detach the bacteria from the retrievals; an aliquot of 100 μL was taken and added to 1900 μL of fresh Mueller-Hinton II broth, and incubated at 37° C. for 24 hr. The concentration of bacteria was then determined by measuring its absorbance at 600 nm (OD 600).

All mice in both control and VPE groups showed similar magnitude of bioluminescence at 5 minutes after being injected subcutaneously. At 3 hr, all mice in the control group showed statistically significant higher magnitude of bioluminescence than those in the VPE group (indicating more bacteria in the control group than that in VPE group). No bioluminescence was detected in the VPE group after 48 hr, while high bioluminescence was detected at 48 hr in the control group (FIG. 9). Sonication and culturing of the retrievals showed absence of bacteria in the VPE group but high amount of bacteria in the control group.

These results showed that 6 wt % vancomycin-blended UHMWPE was effective against bacteria in this model.

Example 9. Joint Implantation of a Vancomycin-Blended UHMWPE in a Rabbit Acute Infection Model A construct with 6 wt % vancomycin-blended UHMWPE was prepared as described in Example 3. This study was conducted to test the efficacy of vancomycin-blended UHMWPE (VPE) against bioluminescent *S. aureus* (Xen 29) in the knee joint of fully immune-competent New Zealand White Rabbit (NZWR). Ten rabbits were divided equally into a control group and a VPE group (n=5 each). None of the rabbits received pre-operative antibiotics. Each rabbit in the control group received two UHMWPE cylinders without additives (each 3 mm in diameter and 6 mm in length) in the patellofemoral groove, and one beaded titanium rod in the tibial canal (4 mm diameter and 12 mm in length). Each rabbit in the VPE group received two VPE cylinders (each 3 mm in diameter and 6 mm in length) in the patellofemoral groove and one beaded titanium rod in the tibial canal (4 mm diameter and 12 mm in length)

Rabbits in both group received two doses of $5 \times 10^7$ cfu of Xen 29 load in 50 μL 0.9% saline: First dose was injected in the distal tibial canal prior to the insertion of titanium rod, and the second dose was injected into the articular space after closure of the parapatellar incision. No rabbits in both groups received post-operative intravenous antibiotics for the duration of study (3 weeks). Complete blood count (CBC) and chemistry (Vancomycin, Creatinine, BUN, ALT, and ALP) were assessed before surgery, post-operative day 3, day 7, day 14, and day 21.

Post-mortem bioluminescence was measured on the knee of all rabbits. Bioluminescence was measured whenever the rabbits expired, or when the study endpoint was reached (day 21). The knees were then dissected to aseptically separate the femur, quadriceps tendon (including patella and patellar tendon), tibia, titanium rods, and UHMWPE implants. The titanium rods were stained with BacLight® Bacterial Live-Dead Stain and imaged using Two-Photon Microscopy to detect presence of live bacteria. The femur, quadriceps tendon, tibia, and UHMWPE cylinders were separately sonicated in sterile saline and cultured in Mueller-Hinton II broth at 37° C. for 24 hr to detect presence of live bacteria. Micro computed tomography (Micro-CT) was conducted on the tibia of one rabbit in each group to verify the osseointegration between bone and titanium.

All five control rabbits expired within 7 days, before the study endpoint was reached. One rabbit in the VPE group expired at day 7 and another one expired at day 15. All of the rabbits in the control group had positive bioluminescence (live bacteria), while none of the rabbits in the VPE group demonstrated any bioluminescence. A representative figure of the bioluminescence of rabbit knee in the control and treated groups is shown in FIG. 10. No vancomycin was detected in all of the rabbits at any time point (detection limit 10 ng/ml). Kidney functions (Creatinine and BUN) and liver functions (ALT and ALP) remained within normal limit for all rabbits in the VPE group during the duration of the study. All rabbits in the control group showed positive bacterial culture after sonication, while all rabbits in VPE group showed negative bacterial culture after sonication. Two-photon imaging showed on 75±10% bacterial viability for bacteria adhered to the titanium in the control group and 0±1% bacterial viability for bacteria adhered to the titanium in the VPE group. Micro-CT showed prominent osseointegration between bone and titanium for VPE group and minimal osseointegration in the control group.

Example 10. Subcutaneous Implantation of a Vancomycin and Rifampin-Blended UHMWPE in a Chronic Infection (Biofilm) Mice Model A layered construct with a surface layer of 3.3 wt % rifampin and 6.7 wt % vancomycin-blended UHMWPE was prepared as described in Example 6. This study was conducted to test the efficacy of rifampin and vancomycin-blended UHMWPE (RV-PE) against biofilm formed by bioluminescent *S. aureus* (Xen 29) on titanium discs implanted in the dorsal subcutaneous pockets of BL6/C57 fully immune-competent mice. Minimum inhibitory concentration of rifampin against Xen 29 was 0.01 μg/ml. Ten mice were used randomly divided into two groups: Control group (n=5) and RV-PE group (n=5). All mice in this study received a titanium disc (10 mm diameter, one surface covered with titanium bead of 100-300 μm in diameter) with pre-grown Xen 29 biofilm on the beaded surface. Each mouse in the control group received a disc implant made from UHMWPE without therapeutic agents (diameter=6 mm, thickness=3 mm) in the dorsal subcutaneous pocket, while each mouse in the RV-PE group received a disc implant made from RV-PE (diameter=6 mm, thickness=3 mm (1 mm layer of RVPE, 2 mm layer of UHMWPE without additives) in the dorsal subcutaneous pocket. After closure of the surgical incision using a monofilament suture, each mouse received a subcutaneous injection of $5\times10^7$ cfu of Xen 29 in 50 μL 0.9% saline. This bacteria inoculation was performed adjacent to the implants. Bioluminescence was measured 5 minutes after bacterial injection, at 3 hr, 24 hr, and 48 hr. Note that only live bacteria luminesce, and therefore the amount of live bacteria was proportional to the total bioluminescence.

At the end of study (1 week after bacterial injection), all mice were sacrificed and implants were removed aseptically and placed into a sterile 15 cc Falcon tube containing 2 ml 0.9% saline. Falcon tubes containing the retrieved implants and saline were sonicated to detach the bacteria from the explants, an aliquot of 100 μL was added to 1900 μL of fresh Mueller-Hinton II broth, and incubated at 37° C. for 24 hr. Concentration of bacteria was then determined using UV-Vis by measuring its absorbance at 600 nm (OD 600).

All mice in both control and RVPE groups showed similar magnitude of bioluminescence at 5 minutes after being injected subcutaneously (FIG. 11). No bioluminescence was detected in the RVPE group after 1 week, while high bioluminescence was detected in the control group after 1 week. Sonication and culturing of the retrieved implants showed absence of bacteria in the RVPE group but high amount of bacteria in the control group.

These results showed that RV-PE was effective in eliminating clinically relevant biofilm and planktonic bacteria simultaneously in a subcutaneous chronic infection model in the mice.

Example 11. Joint Implantation of a Vancomycin and Rifampin-Blended UHMWPE in a Chronic Infection (Biofilm) Rabbit Model A layered construct with a surface layer of 3.3 wt % rifampin and 6.7 wt % vancomycin-blended UHMWPE was prepared as described in Example 6. This study was conducted to test the efficacy of rifampin and vancomycin-blended therapeutic UHMWPE (RV-PE) against biofilm made by bioluminescent *S. aureus* (Xen 29) in the knee joint of fully immune-competent New Zealand White Rabbit (NZWR). Twelve rabbits were used divided randomly into a control group (n=6) and an RVPE group (n=6 each). None of the rabbits received pre-operative antibiotics. Each rabbit in the control group received two cylinders made of UHMWPE without additives (3 mm in diameter and 6 mm in length) in the patellofemoral groove, and one beaded titanium rod covered with a biofilm of Xen 29 cultured in vitro for 48 hours in the tibial canal (4 mm diameter and 12 mm in length). Each rabbit in the RVPE group received two cylinders made of therapeutic UHMWPE (each 3 mm in diameter and 6 mm in length –1 mm layer of RVPE and 5 mm of UHMWPE without additives made as described in Example 5) in the patellofemoral groove and one beaded titanium rod covered with a biofilm of Xen 29 cultured in vitro for 48 hours in the tibial canal (4 mm diameter and 12 mm in length).

No rabbits in both groups received post-operative intravenous antibiotics for the duration of study (3 weeks). Complete blood count (CBC) and chemistry (Creatinine, BUN, ALT, and ALP) were assessed before surgery, post-operative day 3, 7, 14, and 21. Post-mortem biolumines-cence was measured on the superficially dissected knee of all rabbits. Bioluminescence was measured whenever the rabbits expired, or when the study endpoint was reached.

After bioluminescence was measured, the knees were dissected to aseptically separate the femur, quadriceps tendon (including patella and patellar tendon), tibia, titanium rods, and UHMWPE implants. The titanium rods were stained with BacLight® Bacterial Live-Dead Stain and imaged using Two-Photon Microscopy to detect presence of live bacteria. The femur, quadriceps tendon, tibia, and UHMWPE cylinders were separately sonicated in sterile saline and cultured in Mueller-Hinton II broth at 37° C. for 24 hr to detect presence of live bacteria. Micro computed tomography (Micro-CT) was conducted on the tibia of one rabbit in each group to verify the osseointegration between bone and titanium.

No rabbits in the RV-PE group expired during the length of the study (21 days). Five out of six rabbits in the control group died within one week and the last one died at day 14. Liver function enzymes (ALP, ALT) and kidney function markers (Creatinine, BUN) were within normal limits for all rabbits in the RV-PE group throughout the study. No bioluminescence was detected in the knee of any rabbits in the RV-PE group, while positive bioluminescence was detected in the knee of all rabbits in the control group (FIG. 12). Two photon fluorescence imaging of the titanium plugs explanted from the rabbits and stained with live-dead stains showed on average 85% bacterial viability in the control group and no detectable bacterial viability in the RV-PE group (FIG. 13, green indicates viable bacteria, red indicates dead bacteria).

These results indicated that therapeutic UHMWPE implants were able to eliminate biofilm in a peri-prosthetic joint infection model in the rabbit.

Example 12. Layered Direct Compression Molding of a Therapeutic Agent-Blended UHMWPE with UHMWPE without Therapeutic Agent (1)

Rifampin and vancomycin-blended UHMWPE was prepared as described above in Example 6. 3 gram of the blend was spread evenly on the flat base of the female part of a rectangular stainless steel mold (5 cm×8 cm). The thickness of the evenly spread mixture was about 1.3 mm. 30 grams of UHMWPE without additives was then added on top of the blended layer and spread evenly. The male portion of the mold, which had a contoured surface to mimic the articulating surface of a tibial insert, was then contacted with the layered powder.

The therapeutic agent-blended UHMWPE layered onto UHMWPE without additives was consolidated at 170° C. for 10 min at 20 MPa. The platens were then cooled down with air down to approximately 162° C. and then cooled down with water starting at approximately 156° C. down to about room temperature.

The resulting consolidated, layered, therapeutic UHMWPE direct compression molded into the approximate shape of a tibial insert is shown in FIG. 11-1. The therapeutic agent blended UHMWPE was designed to be on the backside surface of the tibial insert.

Example 13. Layered Direct Compression Molding of a Therapeutic Agent-Blended UHMWPE with UHMWPE without Therapeutic Agent (2)

Rifampin and vancomycin-blended UHMWPE was prepared as described above in Example 6. To manufacture an acetabular cup implant preform, a stainless steel mold with a female cavity having a desired outer diameter and cylindrical walls above the hemispherical cavity was used, while the male part of the mold was flat. 58 grams of UHMWPE without additives was added into the female cavity up until 2 mm above the rim of the hemisphere. 6 grams of rifampin and vancomycin-blended UHMWPE was then layered on top.

The therapeutic agent-blended UHMWPE layered onto UHMWPE without additives was consolidated at 170° C. for 10 min at 20 MPa. The platens were then cooled down with air down to approximately 162° C. and then cooled down with water starting at approximately 156° C. down to about room temperature.

The resulting medical implant preform was machined using a CNC mill such that an articulating (inner) surface with a diameter of 40 mm was created below the rim of the hemisphere (FIG. 15). The therapeutic agent blended UHMWPE was designed to be on the rim surface of the acetabular liner.

Example 14. Tranexamic Acid-Blended UHMWPE

Pin-on-disc (POD) wear testing was performed on cylindrical pins (dia. 9 mm, height 10 mm) at 2 Hz in bovine serum for 1.2 million-cycles (MC). Wear was determined gravimetrically about every 0.16 MC and the wear rate was determined by the weight change from 0.5 to 1.2 MC. To correct for the mass loss due to drug elution, samples with similar dimensions were immersed in bovine serum at static loading for the same period of time. Net wear rate was calculated by subtracting the total mass loss with the mass loss due to drug elution. The wear rate was shown in Table 14-1.

Tranexamic acid was blended with UHMWPE as described in Example 2. These results demonstrated that alternative therapeutic agents could be blended and consolidated with UHMWPE.

TABLE 14-1

Wear rate of tranexamic acid-blended UHMWPE. Percentages indicate the weight percentage of therapeutic agent in the blend. Irradiation after blending and consolidation was performed by gamma irradiation.

| Sample | Net Wear rate (mg/million cycle) |
|---|---|
| UHMWPE without additives | 9.75 ± 0.4 |
| 10% Tranexamic Acid in GUR 1020 | 8.19 ± 1.37 |
| 20% Tranexamic Acid in GUR 1020 | 4.49 ± 0.97 |
| 30% Tranexamic Acid in GUR 1020 | 4.13 ± 0.87 |

Example 15. Mechanical Properties of a Layered Construct Containing a Therapeutic Agent Vancomycin-blended GUR1020 UHMWPE (4 wt % vancomycin) was prepared with the method described in Example 3. A second layered GUR1020 UHMWPE comprising a surface 0.5 mm-thick layer of 3.3 wt % rifampin and 6.7 wt % vancomycin-blended UHMWPE and 9.5 mm-thick bulk layer of UHMWPE without additives was prepared with the method described in Example 6. Double-notched IZOD impact strength was performed on samples machined containing the surface layer (6.35×12.7×63.5 mm, n=5) according to ASTM F-648. The impact toughness is reported as (kJ/m$^2$).

TABLE 15-1

The impact toughness of a UHMWPE uniformly blended with a therapeutic agent and a layered UHMWPE with therapeutic agents in the surface layer.

| Material | Impact Strength (kJ/m$^2$) |
|---|---|
| UHMWPE without additives | 132.8 ± 2.3 |
| 4 wt % Vancomycin | 79.5 ± 3.4 |
| 0.5 mm layer of 3.3% Rifampin and 6.7 wt % Vancomycin on top of Virgin GUR 1020 | 137.5 ± 4.2 |

These results suggested the addition of vancomycin decreased the impact toughness of UHMWPE but using a thin layer of additive-blended UHMWPE recovered the loss in toughness.

Example 16. Two-Stage Revision for Peri-Prosthetic Joint Infection (PJI)

Example of a method of making antibiotic-eluting, load-bearing polymeric materials is provided herein. An antibiotic-eluting polymeric material is made in the shape of a bearing surface, for example, an acetabular liner, and is used in a 'two-stage revision for PJI'. In this method, materials are used in conjunction with bone cement/antibiotic-eluting bone cement as a fixation aid. In this method, the joint is opened, the implants (all non-polymeric parts such as the shell for fixation into the acetabulum and the femoral stem/head and all the polymeric components such as the UHMWPE liner are removed. The joint is then debrided and washed thoroughly. Antibiotic eluting bone cement (polymethyl methacrylate or PMMA) is prepared in the operating room by mixing antibiotics with virgin bone cement and filling the resultant paste into the femoral canal and acetabular faces and forming a spacer to maintain the space in between the two. The wound is closed and the patient is treated with intravenous antibiotics for 4-6 weeks after which the antibiotics are discontinued for at least 2 weeks and the clearance of the infection is confirmed by another aspiration and culture. Once the joint is clear of the infection, the joint is re-operated upon and brand new implants are placed, usually accompanied by the use of antibiotic-eluting bone cement as a fixation aid between the joint implant and bony surfaces commensurate with bone cement's primary role.

An antibiotic-eluting polymeric material made by this method is made in the shape of a bearing surface, for example, an acetabular liner, is used instead of the antibiotic eluting bone cement spacer in the two-stage surgery described previously. This antibiotic-eluting liner is load-bearing and therefore, the patient can be mobilized in a manner consistent with their daily lives while being treated for infection.

Alternatively, an antibiotic-eluting polymeric material made by this method is made in the shape of a bearing surface, for example, an acetabular liner, and is used in a 'liner exchange'. In this method, instead of going through a two-stage surgery, a patient with a suspected and/or confirmed peri-prosthetic joint infection undergoes a single surgery where only the polymeric bearing surface (for example, acetabular liner) is removed, the joint is debrided, washed thoroughly (lavage) and a new bearing surface is placed. In this method, the new liner is made out of the antibiotic-eluting polymeric materials.

Example 17. Single-Stage Revision for Peri-Prosthetic Joint Infection (PJI)

Example of a method of making antibiotic-eluting, load-bearing polymeric materials is provided herein. Example of another method of making antibiotic-eluting, load-bearing polymeric material made by this method is made in the shape of a bearing surface, for example, an acetabular liner, and is used in a 'liner exchange'. In this method, instead of going through a two-stage surgery, a patient with a suspected and/or confirmed peri-prosthetic joint infection undergoes a single surgery where only the polymeric bearing surface (for example, acetabular liner) is removed, the joint is debrided, washed thoroughly (lavage) and a new bearing surface is placed. In this method, the new liner is made out of the antibiotic-eluting polymeric materials. The patient can be mobilized in a manner consistent with their daily lives while being treated for infection.

Example of another method of making antibiotic-eluting, load-bearing polymeric materials is provided herein. An antibiotic-eluting polymeric material is made in the shape of a bearing surface, for example, an acetabular liner, and is used in a 'single-stage revision for PJI'. In this method, materials are used in conjunction with bone cement/antibiotic-eluting bone cement as a fixation aid. In this method, instead of going through the two-stage surgery, a patient with a suspected and/or confirmed peri-prosthetic joint infection can undergo a single surgery where at least some but most often all of the non-polymeric implant components and the polymeric bearing surface (for example, acetabular liner) are removed, the joint is debrided, washed thoroughly (lavage) and new implants including a new bearing surface is placed.

Example 18. Antibiotic-Eluting Polymeric Material for Use as a Small Plug or a Cover An antibiotic-eluting polymeric material made by this method is made in the shape of a small plug ('manhole cover') and is used to pressfit into an acetabular shell (FIG. 16). Commonly, some metallic components that come into contact with bony surfaces have holes to accommodate screws for additional fixation strength and stability. Many of these screw holes do not end up accommodating screws during the operation and are left 'as is'. One or more antibiotic-eluting polymeric materials made by this method is placed into these holes instead of screws. These metallic components, for example, in the case of an acetabular shell, is used together with a bearing surface without antibiotics or with a bearing surface eluting antibiotics.

Alternatively, an antibiotic-eluting polymeric material made by this method is made in the shape of a small plug and is used to pressfit into the bearing surface. For example, a tibial insert, which is the polymeric bearing surface used in a total knee replacement, and is made with small indentations on its backside (which is typically in direct contact with the tibial base tray or cemented into the tibial plateau) into which the small plug fits. The bearing surface is then fits with the antibiotic-eluting plug(s) and placed into a tibial base tray (which comes into contact with the bony surfaces on the tibial side of the implant with or without bone cement as a fixation aid).

Example of another method of making an antibiotic-eluting polymeric material is made in the shape of a small plug and is used in a "liner exchange". In this method, instead of going through a two-stage surgery, a patient with a suspected and/or confirmed peri-prosthetic joint infection undergoes a single surgery where only the polymeric bearing surface (for example, acetabular liner) is removed, the joint is debrided, washed thoroughly (lavage) and a new bearing surface is placed. In this method, the antibiotic-eluting small plugs can be placed into the joint, for example into the acetabular shell and the new liner used is made out of the antibiotic-eluting polymeric materials or the new liner used is made out of conventional polymeric materials that are not antibiotic-eluting. The patient can be mobilized in a manner consistent with their daily lives while being treated for infection.

Example of another method of making an antibiotic-eluting polymeric material is made in the shape of a small plug and is used in a "single stage surgery". In this method, instead of going through the two-stage surgery, a patient with a suspected and/or confirmed peri-prosthetic joint infection can undergo a single surgery where at least some but most often all of the non-polymeric implant components and the polymeric bearing surface (for example, acetabular liner) are removed, the joint is debrided, washed thoroughly (lavage) and new implants including a new bearing surface is placed. In this method, the antibiotic-eluting small plugs can be placed into the joint, for example into the acetabular shell and the new liner used is made out of the antibiotic-eluting polymeric materials or the new liner used is made out of conventional polymeric materials that are not antibiotic-eluting. The patient can be mobilized in a manner consistent with their daily lives while being treated for infection.

Example of another method of making an antibiotic-eluting polymeric material is made in the shape of a small plug and is used in a "primary surgery". In this method, the patient is not suspected and/or confirmed for peri-prosthetic joint infection but may be at increased risk for it such as those patients with diabetes. In this method, the antibiotic-eluting small plugs can be placed into the joint, for example into the acetabular shell and the new liner used is made out of the antibiotic-eluting polymeric materials or the new liner used is made out of conventional polymeric materials that are not antibiotic-eluting. The patient can be mobilized in a manner consistent with their daily lives while obtaining a 'cementless' fixation of their joint implant into their bone without the aid of a fixation aid such as bone cement.

What is claimed is:

1. A method of making an antibiotic-eluting implantable medical device comprising:
   a. providing a first UHMWPE (ultra-high molecular weight polyethylene) and a second UHMWPE;
   b. blending the first UHMWPE with about 6 wt % to about 8 wt % gentamicin;
   c. layering the first UHMWPE blended with gentamicin with the second UHMWPE without gentamicin to form a layered UHMWPEs;
   d. direct compression molding the layered UHMWPEs, thereby obtaining the antibiotic-eluting implantable medical device, wherein the medical device is not permanent and removed after use, and wherein the implanted medical device elutes the antibiotic for at least 36 weeks.

2. A method of making an antibiotic-eluting implantable medical device comprising:
   a. providing a first UHMWPE (ultra-high molecular weight polyethylene) and a second UHMWPE;
   b. blending the first UHMWPE with about 6 wt% to about 8 wt% gentamicin to form a first blended UHMWPE;
   c. layering the first blended UHMWPE with the second UHMWPE without gentamicin to form a layered UHMWPEs;
   d. direct compression molding the layered UHMWPEs, thereby obtaining the antibiotic-eluting implantable medical device, wherein the medical device is not permanent and removed after use, and wherein the implanted medical device elutes the antibiotic for at least 36 weeks.

3. A method of making an antibiotic-eluting implantable medical device comprising:
a. providing a first UHMWPE (ultra-high molecular weight polyethylene);
b. blending the UHMWPE with about 6 wt % to about 8 wt % gentamicin to form the first blended UHMWPE;
c. providing a second UHMWPE;
d. blending the second UHMWPE with di-cumyl peroxide to form the second blended UHMWPE;
e. layering the first and the second blended UHMWPEs to form a layered UHMWPEs;
f. consolidating the layered UHMWPEs, thereby obtaining the antibiotic-eluting implantable medical device, wherein the medical device is not permanent and removed after use, and wherein the implanted medical device elutes the antibiotic for at least 36 weeks.

4. The method according to claim 1, wherein the first and the second UHMWPEs are pre-mixed with antioxidant.

5. The method according to claim 1, wherein the antibiotic-eluting implantable medical device is a tibial insert.

6. The method according to claim 5, wherein the tibial insert is packaged and sterilized.

7. A method of making a tibial insert comprising:
a. providing a first UHMWPE (ultra-high molecular weight polyethylene) and a second UHMWPE;
b. blending the first UHMWPE with about 6 wt % to about 8 wt % gentamicin;
c. layering the first UHMWPE blended with gentamicin with the second UHMWPE without gentamicin to form a layered UHMWPEs;
d. direct compression molding the layered UHMWPEs, thereby obtaining the tibial insert, wherein the tibial insert is not permanent and removed after use, and wherein the implanted tibial insert elutes the antibiotic for at least 36 weeks.

8. A method of making an antibiotic-eluting implantable medical device comprising:
a. providing a UHMWPE (ultra-high molecular weight polyethylene);
b. blending UHMWPE with about 6 wt % to about 8 wt % gentamicin; and
c. direct compression molding the gentamicin-blended UHMWPE, thereby obtaining the antibiotic-eluting implantable device, wherein the medical device is not permanent and removed after use, and wherein the implanted medical device elutes the antibiotic for at least 36 weeks.

* * * * *